United States Patent
Martelange et al.

(10) Patent No.: US 6,303,756 B1
(45) Date of Patent: Oct. 16, 2001

(54) TUMOR ASSOCIATED NUCLEIC ACIDS AND USES THEREFOR

(75) Inventors: Valérie Martelange; Charles De Smet; Thierry Boon-Falleur, all of Brussels (BE)

(73) Assignee: Ludwig Institute for Cancer Research, New York, NY (US)

(*) Notice: Subject to any disclaimer, the term of this patent is extended or adjusted under 35 U.S.C. 154(b) by 0 days.

(21) Appl. No.: 09/567,995

(22) Filed: May 10, 2000

Related U.S. Application Data

(63) Continuation of application No. 09/183,706, filed on Oct. 30, 1998, which is a continuation-in-part of application No. 09/122,989, filed on Jul. 27, 1998.

(51) Int. Cl.[7] .......................... C07K 16/00; C07K 16/18; G01N 33/53; C12Q 1/68; C07H 21/04
(52) U.S. Cl. ..................... 530/387.7; 530/387.1; 530/387.9; 435/6; 435/7.1; 435/7.23; 536/23.1; 536/23.5
(58) Field of Search .............................. 435/6, 69.1, 69.3, 435/91.1, 440, 455, 325, 366, 320.1, 7.1, 7.23; 530/350, 387.1, 387.7, 387.9; 536/23.1, 23.5, 24.3, 24.31, 24.33

(56) References Cited

U.S. PATENT DOCUMENTS

| | | |
|---|---|---|
| 5,342,774 | 8/1994 | Boon et al. . |
| 5,405,940 | 4/1995 | Boon et al. . |
| 5,487,974 | 1/1996 | Boon-Falleur et al. . |
| 5,571,711 | 11/1996 | van der Bruggen et al. . |
| 5,587,289 | 12/1996 | Lurquin et al. . |
| 5,589,334 | 12/1996 | Coulie et al. . |
| 5,610,013 | 3/1997 | Van den eynde et al. . |
| 5,620,886 | 4/1997 | Brichard et al. . |
| 5,629,166 | 5/1997 | van der Bruggen et al. . |
| 5,677,430 | 10/1997 | Goodwin et al. . |

FOREIGN PATENT DOCUMENTS

| | | |
|---|---|---|
| 92/120356 | 11/1992 | WO (WO) . |

OTHER PUBLICATIONS

Traversari et al., *J. Exp. Med.* 176:1453–1457 (1992).
van der Bruggen et al., *Science* 254:1643 (1991).
De Plaen et al., *Immunogenetics* 40:360–369, 1994.
Van den Eynde & Brichard, *Curr. Opin. Immunol.* 7:674–681 (1995).
Coulie et al., *Stem Cells* 13:393–403 (1995).
Van den Eynde & van der Bruggen, *Curr, Opin. Immunol.* 9:684–693 (1997).
Topalian et al., *J. Exp. Med.* 183:1965–1971 (1996).
Thomson et al., *Proc. Natl. Acad. Sci. USA* 92:5845–5849 (1995).
Gilbert et al., *Nature Biotechnol.* 15:1280–1284 (1997).
Thomson et al., *J. Immunol.* 157(2):822–826(1996).
Tam et al., *J. Exp. Med.* 171(1):299–306 (1990).
Allsopp et al., *Fur J. Immunol* 26(8):1951–1959(1996).
Altman et al., *Science* 274:94–96, 1996.
Dunbar et al., *Curr. Biol.* 8:413–416, 1998.
Hubank & Schatz, *Nucl. Acids Res.* 22:5640, 1994.
Brichard et al., *Eur. J. Immunol.* 26;224–230, 1996.
van der Bruggen et al., *Eur. J. Immunol.* 24:3038–3043, 1994.
Herman et al., *Immunogenetics* 43:377–383, 1996.
Parker et al.,*J. Immunol.* 152:163, 1994.
Rammensee et al., *Immunogenetics* 41:178–228, 1995.
Hillier et al., Database EMBL, HS1291592, Acc. No. AA496651, Jul. 3, 1997.
Marra et al., Database EMBL, Acc. No. MMAA70068, Jan. 2, 1977.
Strausberg, Database EMBL, HSAA25285, Acc. No. AA213817, Feb. 3, 1997.
Strausberg, Database EMBL, ID/Acc No. AA807217, Feb. 16, 1998.
Strausberg, Database EMBL, Acc. No. AI052728, Jul. 13, 1998.
Adams et al., Database EMBL, ID/Acc. No. AQ280053, Nov. 23, 1998.
Strausberg, Database EMBL, ID/Acc. No. AA883800, Mar. 30, 1998.
Strausberg, Database EMBL, ID/Acc. No. AA948168, May 5, 1998.
Strausberg, Database EMBL, ID/Acc. No. AI378017, Jan. 28, 1999.
Gupta et al., Cancer Letters, 69(3): 173–180 (1993).
Tuting et al., *Eur J of Immunol*, 27(10): 2702–2707 (1997).
Song et al.,*Anticancer Research*, 16(3a): 1171–1175 (1996).

*Primary Examiner*—Sean McGarry
*Assistant Examiner*—Mark L. Shibuya
(74) *Attorney, Agent, or Firm*—Wolf, Greenfield & Sacks, P.C.

(57) ABSTRACT

The invention describes sdp3.8 tumor associated nucleic acids, including fragments and biologically functional variants thereof. Also included are polypeptides and fragments thereof encoded by such nucleic acids, and antibodies relating thereto. Methods and products also are provided for diagnosing and treating conditions characterized by expression of a sdp3.8 gene product.

18 Claims, No Drawings

SEQUENCE LISTING

<160> NUMBER OF SEQ ID NOS: 43

<210> SEQ ID NO 1
<211> LENGTH: 323
<212> TYPE: DNA
<213> ORGANISM: Homo sapiens

<400> SEQUENCE: 1

```
gatcaaatta gagaggaagg tttgaaatgg caaaaaacaa agtgggcaga tttaccacca      60
attaagaaaa acttttataa agagtccact gccacaagtg ccatgtcaaa agtagaagca     120
gatagttgga ggaaagaaaa ttttaatata acgtgggatg acttgaagga tggggagaaa     180
cgacctatcc caatctacct gcacatttga tgacgccttt caatgttatc ctgaggttat     240
ggaaaacatt aaaaaggcag gttttcaaaa gccaacacct attcagtcac aggcatggcc     300
cattgtgttg caaggaatag atc                                             323
```

<210> SEQ ID NO 2
<211> LENGTH: 20
<212> TYPE: DNA
<213> ORGANISM: Homo sapiens

<400> SEQUENCE: 2

```
tagagaggaa ggtttgaaat                                                  20
```

<210> SEQ ID NO 3
<211> LENGTH: 20
<212> TYPE: DNA
<213> ORGANISM: Homo sapiens

<400> SEQUENCE: 3

```
atgtgcaggt agattgggat                                                  20
```

<210> SEQ ID NO 4
<211> LENGTH: 9
<212> TYPE: PRT
<213> ORGANISM: Homo sapiens

<400> SEQUENCE: 4

Glu Ala Asp Pro Thr Gly His Ser Tyr
1               5

<210> SEQ ID NO 5
<211> LENGTH: 9
<212> TYPE: PRT
<213> ORGANISM: Homo sapiens

<400> SEQUENCE: 5

Ser Ala Tyr Gly Glu Pro Arg Lys Leu
1               5

<210> SEQ ID NO 6
<211> LENGTH: 9
<212> TYPE: PRT
<213> ORGANISM: Homo sapiens

<400> SEQUENCE: 6

Glu Val Asp Pro Ile Gly His Leu Tyr
1               5

<210> SEQ ID NO 7

```
<211> LENGTH: 9
<212> TYPE: PRT
<213> ORGANISM: Homo sapiens

<400> SEQUENCE: 7

Phe Leu Trp Gly Pro Arg Ala Leu Val
1               5

<210> SEQ ID NO 8
<211> LENGTH: 10
<212> TYPE: PRT
<213> ORGANISM: Homo sapiens

<400> SEQUENCE: 8

Met Glu Val Asp Pro Ile Gly His Leu Tyr
1               5                   10

<210> SEQ ID NO 9
<211> LENGTH: 9
<212> TYPE: PRT
<213> ORGANISM: Homo sapiens

<400> SEQUENCE: 9

Ala Ala Arg Ala Val Phe Leu Ala Leu
1               5

<210> SEQ ID NO 10
<211> LENGTH: 8
<212> TYPE: PRT
<213> ORGANISM: Homo sapiens

<400> SEQUENCE: 10

Tyr Arg Pro Arg Pro Arg Arg Tyr
1               5

<210> SEQ ID NO 11
<211> LENGTH: 10
<212> TYPE: PRT
<213> ORGANISM: Homo sapiens

<400> SEQUENCE: 11

Ser Pro Ser Ser Asn Arg Ile Arg Asn Thr
1               5                   10

<210> SEQ ID NO 12
<211> LENGTH: 9
<212> TYPE: PRT
<213> ORGANISM: Homo sapiens

<400> SEQUENCE: 12

Val Leu Pro Asp Val Phe Ile Arg Cys
1               5

<210> SEQ ID NO 13
<211> LENGTH: 10
<212> TYPE: PRT
<213> ORGANISM: Homo sapiens

<400> SEQUENCE: 13

Val Leu Pro Asp Val Phe Ile Arg Cys Val
1               5                   10

<210> SEQ ID NO 14
<211> LENGTH: 9
<212> TYPE: PRT
```

```
<213> ORGANISM: Homo sapiens

<400> SEQUENCE: 14

Glu Glu Lys Leu Ile Val Val Leu Phe
1               5

<210> SEQ ID NO 15
<211> LENGTH: 9
<212> TYPE: PRT
<213> ORGANISM: Homo sapiens

<400> SEQUENCE: 15

Glu Glu Lys Leu Ser Val Val Leu Phe
1               5

<210> SEQ ID NO 16
<211> LENGTH: 10
<212> TYPE: PRT
<213> ORGANISM: Homo sapiens

<400> SEQUENCE: 16

Ala Cys Asp Pro His Ser Gly His Phe Val
1               5                   10

<210> SEQ ID NO 17
<211> LENGTH: 10
<212> TYPE: PRT
<213> ORGANISM: Homo sapiens

<400> SEQUENCE: 17

Ala Arg Asp Pro His Ser Gly His Phe Val
1               5                   10

<210> SEQ ID NO 18
<211> LENGTH: 9
<212> TYPE: PRT
<213> ORGANISM: Homo sapiens

<400> SEQUENCE: 18

Ser Tyr Leu Asp Ser Gly Ile His Phe
1               5

<210> SEQ ID NO 19
<211> LENGTH: 9
<212> TYPE: PRT
<213> ORGANISM: Homo sapiens

<400> SEQUENCE: 19

Ser Tyr Leu Asp Ser Gly Ile His Ser
1               5

<210> SEQ ID NO 20
<211> LENGTH: 9
<212> TYPE: PRT
<213> ORGANISM: Homo sapiens

<400> SEQUENCE: 20

Met Leu Leu Ala Val Leu Tyr Cys Leu
1               5

<210> SEQ ID NO 21
<211> LENGTH: 9
<212> TYPE: PRT
<213> ORGANISM: Homo sapiens
```

```
<400> SEQUENCE: 21

Tyr Met Asn Gly Thr Met Ser Gln Val
1               5

<210> SEQ ID NO 22
<211> LENGTH: 9
<212> TYPE: PRT
<213> ORGANISM: Homo sapiens

<400> SEQUENCE: 22

Ala Phe Leu Pro Trp His Arg Leu Phe
1               5

<210> SEQ ID NO 23
<211> LENGTH: 9
<212> TYPE: PRT
<213> ORGANISM: Homo sapiens

<400> SEQUENCE: 23

Ser Glu Ile Trp Arg Asp Ile Asp Phe
1               5

<210> SEQ ID NO 24
<211> LENGTH: 9
<212> TYPE: PRT
<213> ORGANISM: Homo sapiens

<400> SEQUENCE: 24

Tyr Glu Ile Trp Arg Asp Ile Asp Phe
1               5

<210> SEQ ID NO 25
<211> LENGTH: 15
<212> TYPE: PRT
<213> ORGANISM: Homo sapiens

<400> SEQUENCE: 25

Gln Asn Ile Leu Leu Ser Asn Ala Pro Leu Gly Pro Gln Phe Pro
1               5                   10                  15

<210> SEQ ID NO 26
<211> LENGTH: 15
<212> TYPE: PRT
<213> ORGANISM: Homo sapiens

<400> SEQUENCE: 26

Asp Tyr Ser Tyr Leu Gln Asp Ser Asp Pro Asp Ser Phe Gln Asp
1               5                   10                  15

<210> SEQ ID NO 27
<211> LENGTH: 10
<212> TYPE: PRT
<213> ORGANISM: Homo sapiens

<400> SEQUENCE: 27

Glu Ala Ala Gly Ile Gly Ile Leu Thr Val
1               5                   10

<210> SEQ ID NO 28
<211> LENGTH: 9
<212> TYPE: PRT
<213> ORGANISM: Homo sapiens

<400> SEQUENCE: 28
```

Ala Ala Gly Ile Gly Ile Leu Thr Val
1               5

<210> SEQ ID NO 29
<211> LENGTH: 9
<212> TYPE: PRT
<213> ORGANISM: Homo sapiens

<400> SEQUENCE: 29

Ile Leu Thr Val Ile Leu Gly Val Leu
1               5

<210> SEQ ID NO 30
<211> LENGTH: 9
<212> TYPE: PRT
<213> ORGANISM: Homo sapiens

<400> SEQUENCE: 30

Lys Thr Trp Gly Gln Tyr Trp Gln Val
1               5

<210> SEQ ID NO 31
<211> LENGTH: 9
<212> TYPE: PRT
<213> ORGANISM: Homo sapiens

<400> SEQUENCE: 31

Ile Thr Asp Gln Val Pro Phe Ser Val
    1               5

<210> SEQ ID NO 32
<211> LENGTH: 9
<212> TYPE: PRT
<213> ORGANISM: Homo sapiens

<400> SEQUENCE: 32

Tyr Leu Glu Pro Gly Pro Val Thr Ala
1               5

<210> SEQ ID NO 33
<211> LENGTH: 10
<212> TYPE: PRT
<213> ORGANISM: Homo sapiens

<400> SEQUENCE: 33

Leu Leu Asp Gly Thr Ala Thr Leu Arg Leu
1               5                   10

<210> SEQ ID NO 34
<211> LENGTH: 10
<212> TYPE: PRT
<213> ORGANISM: Homo sapiens

<400> SEQUENCE: 34

Val Leu Tyr Arg Tyr Gly Ser Phe Ser Val
1               5                   10

<210> SEQ ID NO 35
<211> LENGTH: 9
<212> TYPE: PRT
<213> ORGANISM: Homo sapiens

<400> SEQUENCE: 35

Leu Tyr Val Asp Ser Leu Phe Phe Leu
1               5

<210> SEQ ID NO 36
<211> LENGTH: 12
<212> TYPE: PRT
<213> ORGANISM: Homo sapiens

<400> SEQUENCE: 36

Lys Ile Ser Gly Gly Pro Arg Ile Ser Tyr Pro Leu
1               5                   10

<210> SEQ ID NO 37
<211> LENGTH: 9
<212> TYPE: PRT
<213> ORGANISM: Homo sapiens

<400> SEQUENCE: 37

Tyr Met Asp Gly Thr Met Ser Gln Val
1               5

<210> SEQ ID NO 38
<211> LENGTH: 12
<212> TYPE: PRT
<213> ORGANISM: Homo sapiens

<400> SEQUENCE: 38

Met Ala Lys Asn Lys Val Gly Arg Phe Thr Thr Asn
1               5                   10

<210> SEQ ID NO 39
<211> LENGTH: 35
<212> TYPE: PRT
<213> ORGANISM: Homo sapiens

<400> SEQUENCE: 39

Met Ser Lys Val Glu Ala Asp Ser Trp Arg Lys Glu Asn Phe Asn Ile
1               5                   10                  15

Thr Trp Asp Asp Leu Lys Asp Gly Glu Lys Arg Pro Ile Pro Ile Tyr
                20                  25                  30

Leu His Ile
        35

<210> SEQ ID NO 40
<211> LENGTH: 50
<212> TYPE: PRT
<213> ORGANISM: Homo sapiens

<400> SEQUENCE: 40

Met Gly Arg Asn Asp Leu Ser Gln Ser Thr Cys Thr Phe Asp Asp Ala
1               5                   10                  15

Phe Gln Cys Tyr Pro Glu Val Met Glu Asn Ile Lys Lys Ala Gly Phe
                20                  25                  30

Gln Lys Pro Thr Pro Ile Gln Ser Gln Ala Trp Pro Ile Val Leu Gln
            35                  40                  45

Gly Ile
        50

<210> SEQ ID NO 41
<211> LENGTH: 36
<212> TYPE: PRT
<213> ORGANISM: Homo sapiens

<400> SEQUENCE: 41

```
Met Thr Pro Phe Asn Val Ile Leu Arg Leu Trp Lys Thr Leu Lys Arg
1               5                   10                  15

Gln Val Phe Lys Ser Gln His Leu Phe Ser His Arg His Gly Pro Leu
                20                  25                  30

Cys Cys Lys Glu
        35

<210> SEQ ID NO 42
<211> LENGTH: 2365
<212> TYPE: DNA
<213> ORGANISM: H. sapiens
<220> FEATURE:
<221> NAME/KEY: CDS
<222> LOCATION: (208)...(2151)

<400> SEQUENCE: 42
ttggtaccga gctcggatcc ctagtaacgg ccgccagtgt gctggaaaga gtgggcggga      60
tagagagcgt gggcgggggg gctagcctcg tgcgggctcc ttaagtagcg gctgcgtggc     120
ttccctggca cgctagtctt acgacgtcac ggtcaggtgg tgcagagctg gacggcaacg     180
acgtcggacg cgccccttct tggaaca atg tcc cac cac gga gga gct ccc aag     234
                               Met Ser His His Gly Gly Ala Pro Lys
                                 1               5 gcc tct acg tgg gtc gtt gct agt cgg cga agc tcg aca gtg tcc cga       282
Ala Ser Thr Trp Val Val Ala Ser Arg Arg Ser Ser Thr Val Ser Arg
 10              15                  20                  25 gcg cca gag agg agg ccg gcg gag gag ttg aat cga aca ggt cct gag       330
Ala Pro Glu Arg Arg Pro Ala Glu Glu Leu Asn Arg Thr Gly Pro Glu
             30                  35                  40 gga tat agt gtc ggc aga ggt ggt cgc tgg aga ggc acc tct agg ccc       378
Gly Tyr Ser Val Gly Arg Gly Gly Arg Trp Arg Gly Thr Ser Arg Pro
         45                  50                  55 ccg gag gcc gtg gcc gct ggt cac gag gaa ctg ccg ctg tgt ttt gct       426
Pro Glu Ala Val Ala Ala Gly His Glu Glu Leu Pro Leu Cys Phe Ala
     60                  65                  70 ttg aag agc cac ttt gtt ggc gcg gta atc ggt cgt ggt ggg tca aaa       474
Leu Lys Ser His Phe Val Gly Ala Val Ile Gly Arg Gly Gly Ser Lys
 75                  80                  85 ata aag aat ata caa agt aca aca aac acc aca atc caa ata ata caa       522
Ile Lys Asn Ile Gln Ser Thr Thr Asn Thr Thr Ile Gln Ile Ile Gln
             95                  100                 105
 90 gaa caa cca gaa tca tta gtc aaa att ttt ggc agc aag gca atg caa       570
Glu Gln Pro Glu Ser Leu Val Lys Ile Phe Gly Ser Lys Ala Met Gln
         110                 115                 120 acg aaa gca aaa gca gtg ata gac aat ttt gtt aaa aag cta gaa gaa       618
Thr Lys Ala Lys Ala Val Ile Asp Asn Phe Val Lys Lys Leu Glu Glu
     125                 130                 135 aat tac aat tca gaa tgc gga att gat act gca ttc caa cct tct gtt       666
Asn Tyr Asn Ser Glu Cys Gly Ile Asp Thr Ala Phe Gln Pro Ser Val
 140                 145                 150 gga aaa gat gga agc aca gat aac aat gtt gtt gca gga gat cgg cca       714
Gly Lys Asp Gly Ser Thr Asp Asn Asn Val Val Ala Gly Asp Arg Pro
         155                 160                 165 ttg ata gat tgg gat caa att aga gag gaa ggt ttg aaa tgg caa aaa       762
Leu Ile Asp Trp Asp Gln Ile Arg Glu Glu Gly Leu Lys Trp Gln Lys
170                  175                 180                 185 aca aag tgg gca gat tta cca cca att aag aaa aac ttt tat aaa gag       810
Thr Lys Trp Ala Asp Leu Pro Pro Ile Lys Lys Asn Phe Tyr Lys Glu
                 190                 195                 200 tcc act gcc aca agt gcc atg tca aaa gta gaa gca gat agt tgg agg      858
```

-continued

```
                Ser Thr Ala Thr Ser Ala Met Ser Lys Val Glu Ala Asp Ser Trp Arg
                        205                 210                 215 aaa gaa aat ttt aat ata acg tgg gat gac ttg aag gat ggg gag aaa              906
Lys Glu Asn Phe Asn Ile Thr Trp Asp Asp Leu Lys Asp Gly Glu Lys
            220                 225                 230 cga cct atc ccc aat cct acc tgc aca ttt gat gac gcc ttt caa tgt              954
Arg Pro Ile Pro Asn Pro Thr Cys Thr Phe Asp Asp Ala Phe Gln Cys
235                 240                 245 tat cct gag gtt atg gaa aac att aaa aag gca ggt ttt caa aag cca             1002
Tyr Pro Glu Val Met Glu Asn Ile Lys Lys Ala Gly Phe Gln Lys Pro
250                 255                 260                 265 aca cct att cag tca cag gca tgg ccc att gtg ttg caa gga ata gat             1050
Thr Pro Ile Gln Ser Gln Ala Trp Pro Ile Val Leu Gln Gly Ile Asp
            270                 275                 280 ctt ata gga gta gcc cag act gga aca gga aag aca ttg tgt tat tta             1098
Leu Ile Gly Val Ala Gln Thr Gly Thr Gly Lys Thr Leu Cys Tyr Leu
                285                 290                 295 atg cct gga ttt att cat ctg gtc ctt caa ccc agc ctt aaa ggt caa             1146
Met Pro Gly Phe Ile His Leu Val Leu Gln Pro Ser Leu Lys Gly Gln
            300                 305                 310 agg aat aga ccc ggc atg tta gtt cta act ccc act cgg gaa tta gca             1194
Arg Asn Arg Pro Gly Met Leu Val Leu Thr Pro Thr Arg Glu Leu Ala
315                 320                 325 ctt caa gta gaa gga gaa tgt tgc aaa tat tca tat aaa ggg ctt cgg             1242
Leu Gln Val Glu Gly Glu Cys Cys Lys Tyr Ser Tyr Lys Gly Leu Arg
330                 335                 340                 345 agt gtt tgt gta tat ggt ggt gga aat aga gat gaa caa ata gaa gag             1290
Ser Val Cys Val Tyr Gly Gly Gly Asn Arg Asp Glu Gln Ile Glu Glu
                350                 355                 360 ctt aaa aaa ggt gta gat atc ata att gca act ccc gga aga ttg aat             1338
Leu Lys Lys Gly Val Asp Ile Ile Ile Ala Thr Pro Gly Arg Leu Asn
            365                 370                 375 gat ctg caa atg agt aac ttc gtc aat ctg aag aat ata acc tac ttg             1386
Asp Leu Gln Met Ser Asn Phe Val Asn Leu Lys Asn Ile Thr Tyr Leu
            380                 385                 390 gtt tta gat gaa gca gac aag atg ttg gac atg gga ttt gaa ccc cag             1434
Val Leu Asp Glu Ala Asp Lys Met Leu Asp Met Gly Phe Glu Pro Gln
395                 400                 405 ata atg aag att ttg tta gat gtg cgc cca gat agg cag aca gtt atg             1482
Ile Met Lys Ile Leu Leu Asp Val Arg Pro Asp Arg Gln Thr Val Met
410                 415                 420                 425 acc agt gct aca tgg cct cat tca gtt cat cgc ctc gca caa tct tat             1530
Thr Ser Ala Thr Trp Pro His Ser Val His Arg Leu Ala Gln Ser Tyr
                430                 435                 440 ttg aaa gaa cca atg att gtc tat gtt ggt aca ttg gat cta gtt gct             1578
Leu Lys Glu Pro Met Ile Val Tyr Val Gly Thr Leu Asp Leu Val Ala
            445                 450                 455 gta agt tca gtg aag caa aat ata att gta acc acc gag gaa gag aaa             1626
Val Ser Ser Val Lys Gln Asn Ile Ile Val Thr Thr Glu Glu Glu Lys
            460                 465                 470 tgg agt cac atg caa act ttt cta cag agt atg tca tcc aca gac aaa             1674
Trp Ser His Met Gln Thr Phe Leu Gln Ser Met Ser Ser Thr Asp Lys
475                 480                 485 gtc att gtc ttc gtt tct cga aaa gct gtt gcg gat cac tta tca agt             1722
Val Ile Val Phe Val Ser Arg Lys Ala Val Ala Asp His Leu Ser Ser
490                 495                 500                 505 gac cta ata ctt gga aat ata tca gta gag tct ctg cat gga gat aga             1770
Asp Leu Ile Leu Gly Asn Ile Ser Val Glu Ser Leu His Gly Asp Arg
            510                 515                 520
```

```
                                                          -continued gaa cag aga gat cgg gag aaa gca tta gag aac ttt aaa aca ggc aaa    1818
Glu Gln Arg Asp Arg Glu Lys Ala Leu Glu Asn Phe Lys Thr Gly Lys
            525                 530                 535 gtg aga ata cta att gca act gat cta gcc tct aga gga ctt gat gtc    1866
Val Arg Ile Leu Ile Ala Thr Asp Leu Ala Ser Arg Gly Leu Asp Val
        540                 545                 550 cat gac gtt aca cat gtc tat aat ttt gac ttt cca cgg aat att gaa    1914
His Asp Val Thr His Val Tyr Asn Phe Asp Phe Pro Arg Asn Ile Glu
    555                 560                 565 gaa tac gta cac cga ata ggg cgc acg gga aga gca ggg agg act ggt    1962
Glu Tyr Val His Arg Ile Gly Arg Thr Gly Arg Ala Gly Arg Thr Gly
570                 575                 580                 585 gtt tcc att aca act ttg act aga aat gat tgg agg gtt gcc tct gaa    2010
Val Ser Ile Thr Thr Leu Thr Arg Asn Asp Trp Arg Val Ala Ser Glu
            590                 595                 600 ttg att aat att ctg gaa aga gca aat cag agt att cca gag gag ctt    2058
Leu Ile Asn Ile Leu Glu Arg Ala Asn Gln Ser Ile Pro Glu Glu Leu
        605                 610                 615 gta tca atg gct gag agg ttt gag gca cat caa cgg aaa agg gaa atg    2106
Val Ser Met Ala Glu Arg Phe Glu Ala His Gln Arg Lys Arg Glu Met
    620                 625                 630 gaa aga aaa atg gaa aga cct caa gga agg ccc aag aag ttt cat         2151
Glu Arg Lys Met Glu Arg Pro Gln Gly Arg Pro Lys Lys Phe His
635                 640                 645 taatgtcttc tgtactagtg gggtagagaa ttcaagattt tttagaaata tagtaagaca  2211
gaagtattgg acatgttggc agtatgaaga gaccggactg atttgactga ttcttaaaat  2271
aatagtgttt gaaaatatag aatccagtgt tttatacttt ctttaataaa aatagaagta  2331
tttaaactta aaaaaaaaaa aaaaaaaaaa aaaa                              2365

<210> SEQ ID NO 43
<211> LENGTH: 648
<212> TYPE: PRT
<213> ORGANISM: H. sapiens

<400> SEQUENCE: 43

Met Ser His His Gly Gly Ala Pro Lys Ala Ser Thr Trp Val Val Ala
1               5                   10                  15

Ser Arg Arg Ser Ser Thr Val Ser Arg Ala Pro Glu Arg Arg Pro Ala
            20                  25                  30

Glu Glu Leu Asn Arg Thr Gly Pro Glu Gly Tyr Ser Val Gly Arg Gly
        35                  40                  45

Gly Arg Trp Arg Gly Thr Ser Arg Pro Pro Glu Ala Val Ala Ala Gly
    50                  55                  60

His Glu Glu Leu Pro Leu Cys Phe Ala Leu Lys Ser His Phe Val Gly
65                  70                  75                  80

Ala Val Ile Gly Arg Gly Gly Ser Lys Ile Lys Asn Ile Gln Ser Thr
                85                  90                  95

Thr Asn Thr Thr Ile Gln Ile Ile Gln Glu Gln Pro Glu Ser Leu Val
            100                 105                 110

Lys Ile Phe Gly Ser Lys Ala Met Gln Thr Lys Ala Lys Ala Val Ile
        115                 120                 125

Asp Asn Phe Val Lys Lys Leu Glu Glu Asn Tyr Asn Ser Glu Cys Gly
    130                 135                 140

Ile Asp Thr Ala Phe Gln Pro Ser Val Gly Lys Asp Gly Ser Thr Asp
145                 150                 155                 160

Asn Asn Val Val Ala Gly Asp Arg Pro Leu Ile Asp Trp Asp Gln Ile
```

-continued

```
                165                 170                 175
Arg Glu Glu Gly Leu Lys Trp Gln Lys Thr Lys Trp Ala Asp Leu Pro
            180                 185                 190
Pro Ile Lys Lys Asn Phe Tyr Lys Glu Ser Thr Ala Thr Ser Ala Met
        195                 200                 205
Ser Lys Val Glu Ala Asp Ser Trp Arg Lys Glu Asn Phe Asn Ile Thr
210                 215                 220
Trp Asp Asp Leu Lys Asp Gly Glu Lys Arg Pro Ile Pro Asn Pro Thr
225                 230                 235                 240
Cys Thr Phe Asp Asp Ala Phe Gln Cys Tyr Pro Glu Val Met Glu Asn
                245                 250                 255
Ile Lys Lys Ala Gly Phe Gln Lys Pro Thr Pro Ile Gln Ser Gln Ala
            260                 265                 270
Trp Pro Ile Val Leu Gln Gly Ile Asp Leu Ile Gly Val Ala Gln Thr
        275                 280                 285
Gly Thr Gly Lys Thr Leu Cys Tyr Leu Met Pro Gly Phe Ile His Leu
        290                 295                 300
Val Leu Gln Pro Ser Leu Lys Gly Gln Arg Asn Arg Pro Gly Met Leu
305                 310                 315                 320
Val Leu Thr Pro Thr Arg Glu Leu Ala Leu Gln Val Glu Gly Glu Cys
                325                 330                 335
Cys Lys Tyr Ser Tyr Lys Gly Leu Arg Ser Val Cys Val Tyr Gly Gly
            340                 345                 350
Gly Asn Arg Asp Glu Gln Ile Glu Glu Leu Lys Lys Gly Val Asp Ile
        355                 360                 365
Ile Ile Ala Thr Pro Gly Arg Leu Asn Asp Leu Gln Met Ser Asn Phe
370                 375                 380
Val Asn Leu Lys Asn Ile Thr Tyr Leu Val Leu Asp Glu Ala Asp Lys
385                 390                 395                 400
Met Leu Asp Met Gly Phe Glu Pro Gln Ile Met Lys Ile Leu Leu Asp
                405                 410                 415
Val Arg Pro Asp Arg Gln Thr Val Met Thr Ser Ala Thr Trp Pro His
            420                 425                 430
Ser Val His Arg Leu Ala Gln Ser Tyr Leu Lys Glu Pro Met Ile Val
        435                 440                 445
Tyr Val Gly Thr Leu Asp Leu Val Ala Val Ser Ser Val Lys Gln Asn
        450                 455                 460
Ile Ile Val Thr Thr Glu Glu Lys Trp Ser His Met Gln Thr Phe
465                 470                 475                 480
Leu Gln Ser Met Ser Ser Thr Asp Lys Val Ile Val Phe Val Ser Arg
                485                 490                 495
Lys Ala Val Ala Asp His Leu Ser Ser Asp Leu Ile Leu Gly Asn Ile
            500                 505                 510
Ser Val Glu Ser Leu His Gly Asp Arg Glu Gln Arg Asp Arg Glu Lys
        515                 520                 525
Ala Leu Glu Asn Phe Lys Thr Gly Lys Val Arg Ile Leu Ile Ala Thr
        530                 535                 540
Asp Leu Ala Ser Arg Gly Leu Asp Val His Asp Val Thr His Val Tyr
545                 550                 555                 560
Asn Phe Asp Phe Pro Arg Asn Ile Glu Glu Tyr Val His Arg Ile Gly
                565                 570                 575
Arg Thr Gly Arg Ala Gly Arg Thr Gly Val Ser Ile Thr Thr Leu Thr
            580                 585                 590
```

```
Arg Asn Asp Trp Arg Val Ala Ser Glu Leu Ile Asn Ile Leu Glu Arg
        595                 600                 605

Ala Asn Gln Ser Ile Pro Glu Glu Leu Val Ser Met Ala Glu Arg Phe
        610                 615                 620

Glu Ala His Gln Arg Lys Arg Glu Met Glu Arg Lys Met Glu Arg Pro
625                 630                 635                 640

Gln Gly Arg Pro Lys Lys Phe His
                645
```

TUMOR ASSOCIATED NUCLEIC ACIDS AND USES THEREFOR

RELATED APPLICATION

This application is a divisional of application Ser. No. 09/183,706, filed Oct. 30, 1998, entitled TUMOR ASSOCIATED NUCLEIC ACIDS AND USES THEREFOR, now, pending; which is a continuation-in-part of U.S. application Ser. No. 09/122,989, filed Jul. 27, 1998.

FIELD OF THE INVENTION

This invention relates to nucleic acid molecules and encoded polypeptides which are expressed preferentially in tumors, particularly in sarcomas. The nucleic acid molecules and encoded polypeptides are useful in, inter alia, diagnostic and therapeutic contexts.

BACKGROUND OF THE INVENTION

The phenotypic changes which distinguish a tumor cell from its normal counterpart are often the result of one or more changes to the genome of the cell. The genes which are expressed in tumor cells, but not in normal counterparts, can be termed "tumor associated" genes. These tumor associated genes are markers for the tumor phenotype. The expression of tumor associated genes can also be an essential event in the process of tumorigenesis. Typically, the host recognizes as foreign the tumor associated genes which are not expressed in normal non-tumorigenic cells. Thus, the expression of tumor associated genes can provoke an immune response against the tumor cells by the host. Tumor associated genes can also be expressed in normal cells within certain tissues without provoking an immune response. In such tissues, expression of the gene and/or presentation of an ordinarily immunologically recognizable fragment of the protein product on the cell surface may not provoke an immune response because the immune system does not "see" the cells inside these immunologically privileged tissues. Examples of immunologically privileged tissues include brain and testis.

The discovery of tumor associated expression of a gene provides a means of identifying a cell as a tumor cell. Diagnostic compounds can be based on the tumor associated gene, and used to determine the presence and location of tumor cells. Further, when the tumor associated gene contributes to an aspect of the tumor phenotype (e.g., unregulated growth or metastasis), the tumor associated gene can be used to provide therapeutics such as antisense nucleic acids which can reduce or substantially eliminate expression of that gene, thereby reducing or substantially eliminating the phenotypic aspect which depends on the expression of the particular tumor associated gene.

As previously noted, the polypeptide products of tumor associated genes can be the targets for host immune surveillance and provoke selection and expansion of one or more clones of cytotoxic T lymphocytes specific for the tumor associated gene product. Examples of this phenomenon include proteins and fragments thereof encoded by the MAGE family of genes, the tyrosinase gene, the Melan-A gene, the BAGE gene, the GAGE gene, the RAGE family of genes, the PRAME gene and the brain glycogen phosphorylase gene, as are detailed below. Thus, tumor associated expression of genes suggests that such genes can encode proteins which will be recognized by the immune system as foreign and thus provide a target for tumor rejection. Such genes encode "tumor rejection antigen precursors", or TRAPs, which may be used to generate therapeutics for enhancement of the immune system response to tumors expressing such genes and proteins.

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J.P. Lipincott Company, 1987), especially chapters 6–10. The interaction of T cells and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. The mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, *Science* 257: 880, 1992; Fremont et al., *Science* 257: 919, 1992; Matsumura et al., *Science* 257: 927, 1992; Latron et al., *Science* 257: 964, 1992.

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *J. Exp. Med.* 176:1453–1457, 1992; van der Bruggen et al., *Science* 254: 1643,1991; De Plaen et al., *Immunogenetics* 40:360–369, 1994 and U.S. Pat. No. 5,342,774 for further information on this family of genes.

In U.S. Pat. No. 5,405,940, the disclosure of which is incorporated by reference, nonapeptides are taught which are presented by the HLA-A1 molecule. The reference teaches that given the known specificity of particular peptides for particular HLA molecules, one should expect a particular peptide to bind one HLA molecule, but no others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. Pat. No. 5,629,166, incorporated by reference, the fact that the MAGE-1 expression product is processed to a second TRA is disclosed. This second TRA is presented by HLA-Cw16 molecules, also known as HLA-C*1601. The disclosure shows that a given TRAP can yield a plurality of TRAs.

In U.S. Pat. No. 5,487,974, incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In U.S. Pat. No. 5,620,886, incorporated herein by reference in its entirety, a second TRA, not derived from tyrosinase is taught to be presented by HLA-A2 molecules. The TRA is derived from a TRAP, but is coded for by a known MAGE gene. This disclosure shows that a particular HLA molecule may present TRAs derived from different sources.

Additional TRAPs are disclosed in U.S. Pat. Nos. 5,571, 711, 5,610,013, 5,587,289 and 5,589,334, as well as PCT publication WO96/10577. The TRAPs are processed to tumor rejection antigens, which are presented by a variety of HLA molecules.

Presently there is a need for additional cancer antigens for development of therapeutics and diagnosis applicable to a greater number of cancer patients having various cancers.

SUMMARY OF THE INVENTION

It now has been discovered that an additional gene, sdp3.8 (HAGE), unrelated to any of the foregoing TRAPs, is expressed in a tumor associated pattern in sarcoma cells. The invention provides isolated sdp3.8 nucleic acid molecules encoding tumor associated polypeptides. The invention also provides expression vectors containing those molecules and host cells transfected with those molecules, as well as isolated polypeptides encoded by the tumor associated nucleic acid molecules (including tumor rejection antigen precursors and fragments of the isolated polypeptides). The foregoing isolated nucleic acid molecules and polypeptides can be used in the diagnosis or treatment of conditions characterized by the expression of a tumor associated gene.

According to one aspect of the invention, an isolated nucleic acid molecule is provided. The molecule hybridizes under stringent conditions to a nucleic acid having a nucleotide sequence as set forth in SEQ ID NO:42. The isolated nucleic acid molecule is a tumor associated polypeptide precursor and codes for a sdp3.8 tumor associated polypeptide, preferably a polypeptide which comprises a polypeptide which binds an HLA molecule. The invention also embraces deletions, additions and substitutions of the foregoing nucleic acids which code for a sdp3.8 tumor associated polypeptide. The invention further embraces nucleic acid molecules that differ from the foregoing isolated nucleic acid molecules in codon sequence due to the degeneracy of the genetic code. The invention also embraces complements of the foregoing nucleic acids. In certain embodiments, the isolated nucleic acid molecule comprises the nucleotide of SEQ ID NO:1 , nucleotides 208–2151 of SEQ ID NO:42, or SEQ ID NO:42. In preferred embodiments, the isolated nucleic acid molecule comprises the coding region of the foregoing nucleic acids.

In another aspect of the invention, an isolated nucleic acid molecule comprising the nucleic acid sequence set forth as SEQ ID NO:1 or nucleotides 208–2151 of SEQ ID NO:42 is provided.

According to another aspect of the invention, an isolated nucleic acid molecule is provided which comprises a unique fragment of nucleotides 1–2340 of SEQ ID NO:42 that is 12 or more nucleotides in length and complements thereof. In preferred embodiments, the fragment is at least 13, 14, 15, 16, 17, 18, 19, 20, 21, 22, 23, 24, 25, 27, 30, 40, 50 or more contiguous nucleotides of the foregoing, and every integer therebetween. In another embodiment, the isolated nucleic acid molecule consists of between 12 and 32 contiguous nucleotides of the foregoing. In still another embodiment, the sequence of the unique fragment includes 1, 2, 3, 4, 5, 6, or 7 contiguous nucleotides nonidentical to the sequence claimed in claim 1. Preferred fragments encode immunogenic fragments of the polypeptide encoded by the sdp3.8 nucleic acid described herein.

Methods for identifying sdp3.8 related nucleic acids, including full-length sdp3.8 cDNAs and sdp3.8 genomic DNAs, are also included in the invention. The methods include contacting a nucleic acid sample (such as a cDNA library, genomic library, genomic DNA isolate, etc.) with a nucleic acid probe or primer derived from a sdp3.8 nucleic acid such as SEQ ID NO:1 or 42. The nucleic acid sample and the probe or primer hybridizes to complementary nucleotide sequences of nucleic acids in the sample, if any are present, allowing detection of sdp3.8 related nucleic acids. Preferably the probe or primer is detectably labeled. The specific conditions, reagents, and the like can be selected by one of ordinary skill in the art to selectively identify sdp3.8 related nucleic acids.

According to yet another aspect of the invention, the invention involves expression vectors, and host cells transformed or transfected with such expression vectors, comprising the nucleic acid molecules described above. The expression vectors optionally include a nucleic acid molecule which codes for an HLA molecule. Of course, an HLA-encoding nucleic acid molecule can also be contained in a separate expression vector. Host cells transformed or transfected with the foregoing expression vectors are also provided.

According to another aspect of the invention, an isolated sdp3.8 polypeptide is provided which is encoded by the foregoing nucleic acid molecules. Fragments of such polypeptides also are provided. Preferably, the fragment of the isolated polypeptide binds to a polypeptide-binding agent. In other preferred embodiments, the fragment of the isolated polypeptide is an immunogenic peptide, such as a fragment which binds to an antibody or a cytotoxic T lymphocyte.

The invention also provides isolated polypeptides which selectively bind a sdp3.8 protein or fragments thereof. Isolated binding polypeptides include antibodies and fragments of antibodies (e.g., Fab, F(ab)$_2$, Fd and antibody fragments which include a CDR3 region which binds selectively to the sdp3.8 proteins of the invention). The isolated binding polypeptides include monoclonal antibodies, humanized antibodies and chimeric antibodies.

In connection with any of the isolated nucleic acids encoding a tumor associated polypeptide as described above, especially a tumor rejection antigen derived from a tumor associated polypeptide, the invention also embraces degenerate nucleic acids that differ from the isolated nucleic acid in codon sequence only due to the degeneracy of the genetic code or complements of any of the foregoing nucleic acids.

According to still another aspect of the invention, methods for diagnosing a disorder characterized by the expression of a tumor associated nucleic acid molecule or a tumor associated polypeptide are provided. The methods involve contacting a biological sample isolated from a subject with an agent that is specific for the tumor associated nucleic acid molecule or an expression product thereof. In certain embodiments, the tumor associated nucleic acid molecule hybridizes under stringent conditions to a molecule having a nucleotide sequence set forth as SEQ ID NO:42. In these certain embodiments, the tumor associated nucleic acid optionally codes for a tumor associated polypeptide. In other embodiments the agent is a binding agent which selectively binds to a sdp3.tumor associated polypeptide, such as an antibody, cytotoxic T lymphocyte, polypeptide, and the like. The methods further involve determining the interaction or binding between the agent and the nucleic acid molecule or expression product thereof as a determination of the disorder. In preferred embodiments, the agent is a nucleic acid molecule comprising a molecule having a nucleotide sequence set forth as SEQ ID NO:42, fragments thereof, and complements thereof. In certain embodiments, the interaction between the agent and the nucleic acid molecule is determined by amplifying at least a portion of the nucleic acid molecule. In preferred embodiments, the agent which binds the tumor associated polypeptide is an antibody. In the foregoing embodiments, the biological sample preferably is isolated from a non-testis tissue. In certain of the foregoing embodiments, the tumor associated nucleic acids and polypeptides are fragments of the foregoing sequences.

The recognition that peptides derived from tumor associated polypeptides may be presented by HLA molecules and recognized by CTLs permits diagnosis of certain disorders. Thus, according to another aspect of the invention, a method for diagnosis of a disorder characterized by expression of a tumor rejection antigen derived from a tumor associated polypeptide is provided. The method involves contacting a biological sample isolated from a subject with an agent that is specific for the tumor rejection antigen derived from a tumor associated polypeptide. The method then provides for determining the interaction between the agent and the tumor rejection antigen derived from a tumor associated polypeptide as a determination of the disorder. In certain embodiments, the tumor rejection antigen derived from a tumor associated polypeptide comprises the amino acid sequence of a polypeptide encoded by SEQ ID NO:42 or nucleic acid molecules which hybridize thereto under stringent conditions. In preferred embodiments, the tumor rejection antigen comprises between 7 and 100 consecutive amino acids (7, 8, 9, 10, 22, 12, 13, 14, 15, and so on including every integer therebetween up to 100) of the foregoing sequences. Preferably, the biological sample is isolated from non-testis tissue. In certain embodiments, the agent is an antibody.

The above-described method provides diagnosis of a disorder based on the presence of tumor associated TRAs. Another aspect of the invention provides methods for diagnosing a disorder characterized by the expression of a tumor rejection antigen derived from a tumor associated polypeptide which forms a complex with HLA molecules. The method involves contacting a biological sample isolated from a subject with an agent that binds the complex and then determining binding between the complex and the agent as a determination of the disorder. In one embodiment, the tumor rejection antigen derived from a sdp3.8 tumor associated polypeptide is a peptide comprising the amino acids of a fragment of a polypeptide encoded by SEQ ID NO:42 or nucleic acid molecules which hybridize thereto under stringent conditions. In preferred embodiments, the tumor rejection antigen comprises between 7 and 100 consecutive amino acids of the foregoing sequences. Preferably, the biological sample is isolated from non-testis tissue. In certain embodiments, the agent is an antibody. Any of the foregoing diagnostic methods can be applied sequentially over time to permit determination of the prognosis or progression of the disorder.

In addition to diagnosis of disorders, treatment of certain disorders is also desirable. According to another aspect of the invention, methods for treating a subject with a disorder characterized by expression of a tumor associated nucleic acid or polypeptide is provided. The method involves administering to the subject an agent which reduces the expression of the sdp3.8 tumor associated nucleic acid or polypeptide to ameliorate the disorder. The agent is administered in an effective amount. In other embodiments, the tumor associated nucleic acid or polypeptide is a nucleic acid and the agent is an antisense nucleic acid. The antisense nucleic acid preferably hybridizes to a tumor associated nucleic acid set forth as SEQ ID NO:1 or nucleic acid molecules which hybridize thereto under stringent conditions and fragments thereof.

In another aspect of the invention, the tumor associated nucleic acid or polypeptide is a tumor rejection antigen and the method involves administering to the subject an amount of an agent which enriches selectively in the subject the presence of complexes of HLA and a tumor associated polypeptide or fragment thereof encoded by SEQ ID NO:42 or nucleic acid molecules which hybridize thereto under stringent conditions, sufficient to ameliorate the disorder. In certain embodiments, the disorder is cancer.

Still other treatment methods provided by the invention involve administering to a subject in need of such treatment an amount of autologous cytolytic T cells sufficient to ameliorate the disorder, wherein the autologous cytolytic T cells are specific for complexes of an HLA molecule and a tumor rejection antigen derived from a sdp3.8 tumor associated polypeptide. Preferably the complexes are formed of HLA and the certain tumor associated peptides as described above. The methods in certain embodiments include removing an immunoreactive cell containing sample from the subject, contacting the immunoreactive cell containing sample to a host cell under conditions favoring production of cytolytic T cells against the tumor associated antigen. The cytolytic T cells are introduced to the subject in an amount effective to lyse cells which express the tumor associated antigen. Preferably the host cell is transformed or transfected with an expression vector comprising the isolated nucleic acid molecule of claim 1 operably linked to a promoter. In certain embodiments the host cell recombinantly expresses an HLA molecule which binds the tumor associated antigen. In other embodiments the host cell endogenously expresses an HLA molecule which binds the tumor associated antigen.

According to another aspect of the invention, a composition is provided. The composition comprises an antisense nucleic acid which binds to a tumor associated nucleic acid set forth as SEQ ID NO:42, and fragments thereof. The antisense nucleic acid reduces the expression of the tumor associated nucleic acid. The composition also includes a pharmaceutically acceptable carrier.

The invention in another aspect involves a kit for detecting the presence of the expression of a tumor associated polypeptide precursor. Such kits employ two or more of the above-described nucleic acid molecules isolated in separate containers and packaged in a single package. In one such kit, a pair of isolated nucleic acid molecules is provided, each of the pair consisting essentially of a molecule selected from the group consisting of a 12–32 nucleotide contiguous segment of SEQ ID NO:42 and complements thereof, and wherein the contiguous segments are nonoverlapping. Preferably, the pair of isolated nucleic acid molecules is constructed and arranged to selectively amplify at least a portion of an isolated nucleic acid molecule which hybridizes under stringent conditions to a molecule selected from the group consisting of the nucleic acid sequence of SEQ ID NO:42, nucleic acid molecules which differ from the above in codon sequence due to the degeneracy of the genetic code and complements thereof. In certain embodiments, the pair of isolated nucleic acid molecules is PCR primers. Preferably one of the primers is a contiguous segment of SEQ ID NO:42 and another of the primers is a complement of another contiguous segment of SEQ ID NO:42.

According to yet another aspect of the invention, methods for producing a tumor associated polypeptide are provided. The methods include providing a nucleic acid molecule comprising a sdp3.8 tumor associated nucleic acid molecule operably linked to a promoter. The tumor associated nucleic acid molecule encodes the tumor associated polypeptide or a fragment thereof, wherein the tumor associated polypeptide is SEQ ID NO:4 or a fragment thereof. The methods also include expressing the nucleic acid molecule in an expression system, and isolating the tumor associated polypeptide or a fragment thereof from the expression system.

The invention in another aspect also provides pharmaceutical preparations containing the agents and/or cells of the preceding paragraphs. In one embodiment, the preparation contains a pharmaceutically effective amount of sdp3.8 polypeptides encoded by the foregoing nucleic acids, or a fragment thereof, that binds an HLA molecule along with pharmaceutically acceptable diluents, carriers or excipients. In another embodiment, the preparation contains a pharmaceutically effective amount of isolated autologous cytolytic T cells specific for complexes of an HLA molecule and a tumor rejection antigen derived from such sdp3.8 polypeptides.

According to another aspect of the invention, the use of isolated sdp3.8 polypeptides or nucleic acids, or fragments thereof, in the manufacture of a medicament is provided. Preferred fragments of the sdp3.8 molecules are described above. The use of antisense nucleic acids which bind to a tumor associated nucleic acid in the manufacture of a medicament is also provided. In certain embodiments, the medicament is an injectable medicament, an oral medicament, or an inhalable medicament.

According to another aspect of the invention, the use of isolated sdp3.8 polypeptides or nucleic acids, or fragments thereof, including antisense nucleic acids, in the manufacture of a medicament for the treatment of cancer is provided.

The invention also embraces functional variants and equivalents of all of the molecules described above.

These and other objects of the invention will be described in further detail in connection with the detailed description of the invention.

DETAILED DESCRIPTION OF THE INVENTION

The examples which follow show the isolation of nucleic acid molecules which code for polypeptides and are expressed preferentially in tumor cells, i.e. which are tumor associated genes. It is believed that the isolated nucleic acid molecules encode sdp3.8 polypeptides because the nucleic acid molecules were initially isolated from expressed mRNA via RT-PCR amplification. Hence, one aspect of the invention is an isolated nucleic acid molecule which includes all or a fragment of the nucleotide sequence set forth in SEQ ID NO:42. This sequence does not encode a previously recognized tumor rejection antigen precursor, such as a MAGE, BAGE, GAGE, RAGE, LB33/MUM-1, PRAME, NAG, MAGE-Xp or brain glycogen phosphorylase sequence, as will be seen by comparing them to the sequence of any of the genes described in the references.

The invention thus involves in one aspect sdp3.8 (HAGE) nucleic acids, encoded polypeptides, functional modifications and variants of the foregoing, useful fragments of the foregoing, as well as therapeutics and diagnostics related thereto.

The invention provides nucleic acid molecules which can code for a sdp3.8 polypeptide and which hybridize under stringent conditions to a nucleic acid molecule consisting of the nucleotide sequence set forth in SEQ ID NO:42. Such nucleic acids are termed tumor associated polypeptide precursors, and may be DNA, RNA, or composed of mixed deoxyribonucleotides and ribonucleotides. The tumor associated polypeptide precursors can also incorporate synthetic non-natural nucleotides.

The invention thus encompasses other tumor associated nucleic acids, some of which may be expressed in normal tissues. A tumor associated nucleic acid or polypeptide is a nucleic acid or polypeptide expressed preferentially in cancer cells, such as tumors including sarcomas, carcinomas, etc. Various methods for determining the expression of a nucleic acid and/or a polypeptide in normal and tumor cells are known to those of skill in the art and are described further below. As used herein, tumor associated polypeptides include proteins, protein fragments, and peptides. In particular, tumor associated polypeptides include TRAPs and TRAs.

The term "stringent conditions" as used herein refers to parameters with which the art is familiar. More specifically, stringent conditions, as used herein, refers to hybridization at 65° C. in hybridization buffer (3.5×SSC, 0.02% Ficoll, 0.02% polyvinyl pyrolidone, 0.02% Bovine Serum Albumin, 25 mM $NaH_2PO_4$ (pH 7), 0.5% SDS, 2 mM EDTA). SSC is 0.15M sodium chloride/0.015M sodium citrate, pH 7; SDS is sodium dodecyl sulphate; and EDTA is ethylenediaminetetracetic acid. After hybridization, the membrane upon which the nucleic acid is transferred is washed at 2×SSC at room temperature and then at 0.1×SSC/ 0.1×SDS at 65° C. SSC is 0.15M sodium chloride/0.15M sodium citrate, pH7; SDS is sodium dodecyl sulphate; and EDTA is ethylenediamine tetraacetic acid. After hybridization, the support upon which the nucleic acid is transferred is washed, for example, in 2×SSC at room temperature and then at 0.1–0.5×SSC/0.1×SDS at temperatures up to 68° C. The foregoing set of hybridization conditions is but one example of stringent hybridization conditions known to one of ordinary skill in the art.

There are other conditions, reagents, and so forth which can be used, which result in stringent hybridization (see, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York). The skilled artisan will be familiar with such conditions, and thus they are not given here. It will be understood, however, that the skilled artisan will be able to manipulate the conditions in a manner to permit the clear identification of homologs and alleles of sdp3.8 nucleic acid molecules of the invention. The skilled artisan also is familiar with the methodology for screening cells, preferably cancer cells, and libraries for expression of such molecules which then are routinely isolated, followed by isolation of the pertinent nucleic acid and sequencing. Thus sdp3.8 nucleic acids including full-length cDNAs and genomic DNAs are provided by the invention.

In general homologs and alleles typically will share at least 40% nucleotide identity and/or at least 50% amino acid identity to the coding region of tumor associated nucleic acids, in some instances will share at least 50% nucleotide identity and/or at least 65% amino acid identity and in still other instances will share at least 60% nucleotide identity and/or at least 75% amino acid identity. Preferred homologs and alleles share nucleotide and amino acid identities with SEQ ID NO:42 and encode polypeptides of greater than 80%, more preferably greater than 90%, still more preferably greater than 95% and most preferably greater than 99% identity. The percent identity can be calculated using various, publicly available software tools developed by NCBI (Bethesda, Md.) that can be obtained through the internet from the National Center for Biotechnology Information website. Exemplary tools include the BLAST system available at the National Center for Biotechnology Information website, which uses algorithms developed by Altschul et al. (*Nucleic Acids Res.* 25:3389–3402, 1997). Pairwise and ClustalW alignments (BLOSUM30 matrix setting) as well as Kyte-Doolittle hydropathic analysis can be obtained using the MacVector sequence analysis software (Oxford Molecular Group). Complements of the foregoing nucleic acids also are embraced by the invention.

Also provided are nucleic acid molecules which include the nucleotide sequence of SEQ ID NO:1 or nucleotides 208–2151 of SEQ ID NO:42, and fragments thereof.

The nucleic acids disclosed herein are useful as probes and amplification primers for determining the expression of sdp3.8 genes according to standard hybridization procedures. The nucleic acids also can be used to express tumor associated polypeptides in vitro or in vivo, by, e.g., operably linking the nucleic acid to a promoter and transcribing and translating the nucleic acid in an expression system. The nucleic acids also can be used to prepare fragments of such polypeptides useful for e.g., preparation of antibodies. Many other uses will be apparent to the skilled artisan.

In screening for related nucleic acids, such as nucleic acid molecules related in nucleotide sequence to sdp3.8, a Southern blot may be performed using the foregoing conditions, together with a radioactive probe (e.g. SEQ ID NO:1). After washing the membrane to which the nucleic acid is finally transferred, the membrane can be placed against x-ray film to detect the radioactive signal. In screening for the expression of tumor associated nucleic acids, Northern blot hybridizations using the foregoing conditions (see also the Examples) can be performed on samples taken from cancer patients or subjects suspected of having a condition characterized by expression of tumor associated nucleic acids. Amplification protocols such as polymerase chain reaction using primers which hybridize to the sequences presented also can be used for detection of the tumor associated nucleic acids or expression products thereof.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:42 or complements thereof, particularly "unique" fragments. A unique fragment is one that is a 'signature' for the larger nucleic acid. It, for example, is long enough to assure that its precise sequence is not found in molecules within the human genome outside of the HAGE (sdp3.8) nucleic acids defined herein (and human alleles). Those of ordinary skill in the art may apply no more than routine procedures to determine if a fragment is unique within the human genome. Unique fragments, however, exclude fragments completely composed of the nucleotide sequences of any of the GenBank accession numbers listed in Table V or other previously published sequences as of the filing date of the priority documents for sequences listed in a respective priority document or the filing date of this application for sequences listed for the first time in this application which overlap the sequences of the invention.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, or for generating immunoassay components. Likewise, unique fragments can be employed to produce nonfused fragments of sdp3.8 polypeptides, useful, for example, in the preparation of antibodies, and in immunoassays. Unique fragments further can be used as antisense molecules to inhibit the expression of sdp3.8 nucleic acids and polypeptides, particularly for therapeutic purposes as described in greater detail below.

As will be recognized by those skilled in the art, the size of the unique fragment will depend upon its conservancy in the genetic code. Thus, some regions of sdp3.8 sequences, such as SEQ ID NO:42, and complements thereof will require longer segments to be unique while others will require only short segments, typically between 12 and 32 nucleotides or more in length (e.g. 12, 13, 14, 15, 16, 17, 18, 19, 20, 21, 22, 23, 24, 25, 26, 27, 28, 29, 30, 31 and 32 or more), up to the entire length of the disclosed sequence. The invention embraces each and every fragment of the sdp3.8 sequence, beginning at the first nucleotide, the second nucleotide and so on, up to 12 nucleotides short of the end, and ending anywhere from nucleotide number 12, 13, 14 and so on, up to the very last nucleotide (provided the sequence is unique as described above).

Many segments of the polypeptide coding region of novel tumor associated nucleic acids, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome. A comparison of the sequence of the fragment to those on known databases typically is all that is necessary, although in vitro confirmatory hybridization and sequencing analysis may be performed.

A unique fragment can be a functional fragment. A functional fragment of a nucleic acid molecule of the invention is a fragment which retains some functional property of the larger nucleic acid molecule, such as coding for a functional polypeptide, binding to proteins, regulating transcription of operably linked nucleic acids, and the like. One of ordinary skill in the art can readily determine using the assays described herein and those well known in the art to determine whether a fragment is a functional fragment of a nucleic acid molecule using no more than routine experimentation.

For any pair of PCR primers constructed and arranged to selectively amplify, for example, a sdp3.8 nucleic acid, a sdp3.8 specific primer may be used. Such a primer is a contiguous stretch of sdp3.8 which hybridizes selectively to sdp3.8 nucleic acids. Such a specific primer would fully hybridize to a contiguous stretch of nucleotides only in sdp3.8 nucleic acids, but would hybridize at most only in part to genes that do not share the nucleotides to which the sdp3.8 specific primer binds. For efficient PCR priming and sdp3.8 nucleic acid identification, the sdp3.8 specific primer should be constructed and arranged so it does not hybridize efficiently at its 3' end to genes other than sdp3.8. Preferably the area of non-identity is at least one to four nucleotides in length and forms the 3' end of the sdp3.8 specific primer. The kinetics of hybridization then will strongly favor hybridization at the 5' end. In this instance, 3' initiated PCR extension will occur only when both the 5' and 3' ends hybridize to the nucleic acid. Exemplary primers include SEQ ID NO:2 and SEQ ID NO:3, which are derived from SEQ ID NO:1. Other exemplary primers can differ from the above by addition or deletion of 1, 2, 3, 4, 5, or more nucleotides from the 5' end of the primer. One of ordinary skill in the art can determine with no more than routine experimentation the preferred primers for selective amplification of sdp3.8 and related genes. Additional methods which can distinguish nucleotide sequences of substantial homology, such as ligase chain reaction ("LCR") and other methods, will be apparent to skilled artisans.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid molecule as used herein is not a naturally occurring chromosome.

The invention also provides isolated polypeptides which include translation products of SEQ ID NO:42, related SAGE (sdp3.8) nucleic acids (such as cDNAs including the full-length coding region of sdp3.8, e.g. SEQ ID NO:42) and fragments thereof. Such polypeptides are useful, for example, alone or as fusion proteins to generate antibodies, as a component of an immunoassay, or for determining the binding specificity of HLA molecules and/or CTL clones for sdp3.8 proteins. Tumor associated polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

Thus, as used herein with respect to polypeptides, "isolated" means separated from its native environment and present in sufficient quantity to permit its identification or use. Isolated, when referring to a protein or polypeptide, means, for example: (i) selectively produced by expression of a recombinant nucleic acid or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

A fragment of a sdp3.8 protein, for example, generally has the features and characteristics of fragments including unique fragments as discussed above in connection with nucleic acids. As will be recognized by those skilled in the art, the size of a fragment which is unique will depend upon factors such as whether the fragment constitutes a portion of a conserved protein domain. Thus, some regions of sdp3.8 polypeptides will require longer segments to be unique while others will require only short segments, typically between 5 and 12 amino acids (e.g. 5, 6, 7, 8, 9, 10, 11 and 12 amino acids long).

Unique fragments of a polypeptide preferably are those fragments which retain a distinct functional capability of the polypeptide. Functional capabilities which can be retained in a fragment of a polypeptide include interaction with antibodies, interaction with other polypeptides or fragments thereof, selective binding of nucleic acids, and enzymatic activity. One important activity is the ability to act as a signature for identifying the polypeptide. Another is the ability to complex with HLA and to provoke in a human an immune response. A tumor rejection antigen is an example of a fragment of a tumor associated polypeptide which retains the functional capability of HLA binding and interaction with T lymphocytes. Tumor rejection antigens presented by HLA class I molecules typically are 9 amino acids in length, although peptides of 8, 9 and 10 and more amino acids also retain the capability to interact with HLA and T lymphocytes to an extent effective to provoke a cytotoxic T lymphocyte response (see, e.g., Van den Eynde & Brichard., *Curr. Opin. Immunol.* 7:674–681, 1995; Coulie et al., *Stem Cells* 13:393–403, 1995). Similarly, tumor rejection antigens (e.g., 10–20 amino acids in length) can interact with HLA class II molecules and T helper lymphocytes, provoking proliferation and response of the T helper lymphocytes (see, e.g., Van den Eynde & van der Bruggen, *Curr. Opin. Immunol.* 9:684–693, 1997; Topalian et al., *J. Exp. Med.* 183:1965–1971, 1996).

Those skilled in the art are well versed in methods for selecting unique amino acid sequences, typically on the basis of the ability of the fragment to selectively distinguish the sequence of interest from non-family members. A comparison of the sequence of the fragment to those on known data bases typically is all that is necessary.

The invention embraces variants of the tumor associated polypeptides described above. As used herein, a "variant" of a tumor associated polypeptide is a polypeptide which contains one or more modifications to the primary amino acid sequence of a tumor associated polypeptide. Modifications which create a tumor associated polypeptide variant can be made to a tumor associated polypeptide 1) to reduce or eliminate an activity of the tumor associated polypeptide; 2) to enhance a property of the tumor associated polypeptide, such as protein stability in an expression system or the stability of protein-protein binding; 3) to provide a novel activity or property to a tumor associated polypeptide, such as addition of an antigenic epitope or addition of a detectable moiety; or 4) to provide equivalent or better binding to an HLA molecule. Modifications to a tumor associated polypeptide are typically made to the nucleic acid which encodes the tumor associated polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the tumor associated amino acid sequences, e.g., SEQ ID NOs:43. One of skill in the art will be familiar with methods for predicting the effect on protein conformation of a change in protein sequence, and can thus "design" a variant tumor associated polypeptide according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a tumor associated polypeptide can be proposed and tested to determine whether the variant retains a desired conformation.

In general, variants include tumor associated polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a tumor associated polypeptide by eliminating proteolysis by proteases in an expression system (e.g., dibasic amino acid residues in yeast expression systems in which KEX2 protease activity is present).

Mutations of a nucleic acid which encode a tumor associated polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant tumor associated polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a tumor associated gene or cDNA clone to enhance expression of the polypeptide. The activity of variants of tumor associated polypeptides can be tested by cloning the gene encoding the variant tumor associated polypeptide into a bacterial or mammalian expression vector, introducing the vector into an appropriate host cell, expressing the variant tumor associated polypeptide, and testing for a functional capability of the tumor associated polypeptides as disclosed herein. For example, the variant tumor associated polypeptide can be tested for reaction with autologous or allogeneic sera as disclosed in the Examples. Preparation of other variant polypeptides may favor testing of other activities, as will be known to one of ordinary skill in the art.

The skilled artisan will also realize that conservative amino acid substitutions may be made in sdp3.8 polypeptides to provide functional variants of the foregoing polypeptides, i.e, the variants which the functional capabilities of the sdp3.8 polypeptides. As used herein, a "conservative amino acid substitution" refers to an amino acid substitution which does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, upon determining that a peptide derived from a sdp3.8 polypeptide is presented by a MHC molecule and recognized by CTLs (e.g., as described in the Examples), one can make conservative amino acid substitutions to the amino acid sequence of the peptide, particularly at residues which are thought not to be direct contact points with the MHC molecule. For example, methods for identifying functional variants of HLA class II binding peptides are provided in a published PCT application of Strominger and Wucherpfennig (PCT/US96/03182). Peptides bearing one or more amino acid substitutions also can be tested for concordance with known HLA/MHC motifs prior to synthesis using, e.g. the computer program described by D'Amaro and Drijfhout (D'Amaro et al., *Human Immunol.* 43:13–18, 1995; Drijfhout et al., *Human Immunol.* 43:1–12, 1995) or as described below in the Examples. The substituted peptides can then be tested for binding to the MHC molecule and recognition by CTLs when bound to MHC. These variants can be tested for improved stability and are useful, inter alia, in vaccine compositions.

Functional variants of sdp3.8 polypeptides, i.e., variants of polypeptides which retain the function of the natural polypeptides, can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. For example, exemplary functional variants of the sdp3.8 polypeptides include conservative amino acid substitutions of polypeptides encoded by SEQ ID NO:42. Conservative amino-acid substitutions in the amino acid sequence of sdp3.8 polypeptides to produce functional variants of sdp3.8 polypeptides typically are made by alteration of the nucleic acid encoding a sdp3.8 polypeptide (e.g. SEQ ID NO:42). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a sdp3.8 polypeptide. Where amino acid substitutions are made to a small unique fragment of a sdp3.8 polypeptide, such as a 9 amino acid peptide, the substitutions can be made by directly synthesizing the peptide. The activity of functional variants or fragments of sdp3.8 polypeptides can be tested by cloning the gene encoding the altered sdp3.8 polypeptide into a bacterial or mammalian expression vector, introducing the vector into an appropriate host cell, expressing the altered sdp3.8 polypeptide, and testing for a functional capability of the sdp3.8 polypeptides as disclosed herein.

As mentioned above, the invention embraces antisense oligonucleotides that selectively bind to a tumor associated gene nucleic acid molecule, including those encoding a sdp3.8 protein, to decrease transcription and/or translation of tumor associated genes. This is desirable in virtually any medical condition wherein a reduction in tumor associated gene product expression is desirable, including to reduce any aspect of a malignant cell phenotype attributable to tumor associated gene expression, such as expression of sdp3.8. Antisense molecules, in this manner, can be used to slow down or arrest such aspects of a malignant cell phenotype as found in, inter alia, sarcomas and carcinomas.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:42 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 (Wagner et al., *Nature Biotechnology* 14:840–844, 1996) and, more preferably, at least 15 consecutive bases which are complementary to the target. Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although, SEQ ID NO:42 discloses a cDNA sequence, one of ordinary skill in the art may easily derive the corresponding genomic DNA. Thus, the present invention also provides for antisense oligonucleotides which are complementary to the full length cDNA and/or genomic DNA corresponding to SEQ ID NO:42. Similarly, antisense to allelic or homologous DNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, peptides, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. Modified oligonucleotides also can include base analogs such as C-5 propyne modified bases (Wagner et al., *Nature Biotechnology* 14:840–844, 1996). The present invention, thus, contemplates pharmaceutical preparations containing modified antisense molecules that are complementary to and hybridizable with, under physiological conditions, nucleic acids encoding tumor associated proteins, together with pharmaceutically acceptable carriers.

It will also be recognized from the examples that the invention embraces the use of the sdp3.8 sequences in expression vectors, as well as to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as mouse, hamster, pig, goat, primate, etc. They can be of a wide variety of tissue types, including mast cells, fibroblasts, oocytes and lymphocytes, and they may be primary cells or cell lines. Specific examples include dendritic cells, U293 cells, peripheral blood leukocytes, bone marrow stem cells and embryonic stem cells. The expression vectors require that the pertinent sequence, i.e., those nucleic acids described supra, be operably linked to a promoter.

Especially preferred are nucleic acids encoding a series of epitopes, known as "polytopes". The epitopes can be arranged in sequential or overlapping fashion (see, e. Thomson et al., *Proc. Natl. Acad. Sci. USA* 92:5845–5849, 1995; Gilbert et al., *Nature Biotechnol.* 15:1280–1284, 1997), with or without the natural flanking sequences, and can be separated by unrelated linker sequences if desired. The polytope is processed to generated individual epitopes which are recognized by the immune system for generation of immune responses.

Thus, for example, peptides derived from the polypeptide having an amino acid sequence encoded by the nucleic acid of SEQ ID NO:42, and which are presented by MHC molecules and recognized by CTL or T helper lymphocytes can be combined with peptides from other tumor rejection antigens (e.g. by preparation of hybrid nucleic acids or polypeptides) to form "polytopes". Exemplary tumor associated peptide antigens that can be administered to induce or enhance an immune response are derived from tumor associated genes and encoded proteins including MAGE-1, MAGE-2, MAGE-3, MAGE-4, MAGE-5, MAGE-6, MAGE-7, MAGE-8, MAGE-9,MAGE-10, MAGE-11 , MAGE-12, MAGE-13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1 and CT-7. For example, antigenic peptides characteristic of tumors include those listed in Table I below.

TABLE I

Exemplary Antigens

| Gene | MHC | Peptide | Position | SEQ ID NO: |
|---|---|---|---|---|
| MAGE-1 | HLA-A1 | EADPTGHSY | 161–169 | 4 |
|  | HLA-Cw16 | SAYGEPRKL | 230–238 | 5 |
| MAGE-3 | HLA-A1 | EVDPIGHLY | 168–176 | 6 |
|  | HLA-A2 | FLWGPRALV | 271–279 | 7 |
|  | HLA-B44 | MEVDPIGHLY | 167–176 | 8 |
| BAGE | HLA-Cw16 | AARAVFLAL | 2–10 | 9 |
| GAGE-1, 2 | HLA-Cw16 | YRPRPRRY | 9–16 | 10 |
| RAGE | HLA-B7 | SPSSNRIRNT | 11–20 | 11 |
| GnT-V | HLA-A2 | VLPDVFIRC(V) | 2–10/11 | 12, 13 |
| MUM-1 | HLA-B44 | EEKLIVVLF | exon 2/intron | 14 |
|  |  | EEKLSVVLF (wild type) |  | 15 |
| CDK4 | HLA-A2 | ACDPHSGHFV | 23–32 | 16 |
|  |  | ARDPHSGHFV (wild type) |  | 17 |
| β-catenin | HLA-A24 | SYLDSGIHF | 29–37 | 18 |
|  |  | SYLDSGIHS (wild type) |  | 19 |
| Tyrosinase | HLA-A2 | MLLAVLYCL | 1–9 | 20 |
|  | HLA-A2 | YMNGTMSQV | 369–377 | 21 |
|  | HLA-A2 | YMDGTMSQV | 369–377 | 37 |
|  | HLA-A24 | AFLPWHRLF | 206–214 | 22 |
|  | HLA-B44 | SEIWRDIDF | 192–200 | 23 |
|  | HLA-B44 | YEIWRDIDF | 192–200 | 24 |
|  | HLA-DR4 | QNILLSNAPLGPQFP | 56–70 | 25 |
|  | HLA-DR4 | DYSYLQDSDPDSFQD | 448–462 | 26 |
| Melan-A$^{MART-1}$ | HLA-A2 | (E)AAGIGILTV | 26/27–35 | 27, 28 |
|  | HLA-A2 | ILTVILGVL | 32-40 | 29 |
| gp100$^{Pmel117}$ | HLA-A2 | KTWGQYWQV | 154–162 | 30 |
|  | HLA-A2 | ITDQVPFSV | 209–217 | 31 |
|  | HLA-A2 | YLBPGPVTA | 280–288 | 32 |
|  | HLA-A2 | LLDGTATLRL | 457–466 | 33 |
|  | HLA-A2 | VLYRYGSFSV | 476–485 | 34 |
| PRAME | HLA-A24 | LYVDSLFFL | 301–309 | 35 |
| MAGB-6 | HLA-Cw16 | KISGGPRISYPL | 292–303 | 36 |

See, for example, PCT application publication no. WO96/10577. Other examples will be known to one of ordinary skill in the art (for example, see Coulie, *Stem Cells* 13:393–403, 1995), and can be used in the invention in a like manner as those disclosed herein. One of ordinary skill in the art can prepare polypeptides comprising one or more sdp3.8 peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci USA* 92(13) :5845–5849, 1995; Gilbert et al., *Nature Biotechnol.* 15(12) :1280–1284, 1997; Thomson et al., *J. Immunol.* 157(2) :822–826 1996; Tam et al., *J. Exp. Med.* 171(1):299–306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8) :1951–1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

In instances in which a human HLA class I molecule presents tumor rejection antigens derived from sdp3.8 nucleic acids, the expression vector may also include a nucleic acid sequence coding for the HLA molecule that presents any particular tumor rejection antigen derived from these nucleic acids and polypeptides. Alternatively, the nucleic acid sequence coding for such a HLA molecule can be contained within a separate expression vector. In a situation where the vector contains both coding sequences, the single vector can be used to transfect a cell which does not normally express either one. Where the coding sequences for the tumor rejection antigen precursor and the HLA molecule which presents it are contained on separate expression vectors, the expression vectors can be cotransfected. The tumor rejection antigen precursor coding sequence may be used alone, when, e.g. the host cell already expresses a HLA molecule which presents a TRA derived from sdp3.8 TRAPs. Of course, there is no limit on the particular host cell which can be used. As the vectors which contain the two coding sequences may be used in any antigen-presenting cells if desired, and the gene for tumor rejection antigen precursor can be used in host cells which do not express a HLA molecule which presents a sdp3.8 TRA. Further, cell-free transcription systems may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g. β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined. Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with the initiation of transcription and translation respectively, such as a TATA box, capping sequence, CAAT sequence, and the like.

Especially, such 5' non-transcribing regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences, 5' or 3'. The choice and design of an appropriate vector is within the ability and discretion of one of ordinary skill in the art.

Expression vectors containing all the necessary elements for expression are commercially available and known to those skilled in the art. See *Molecular Cloning: A Laboratory Manual,* J. Sambrook, et al., eds., Second Edition, Cold Spring Harbor Laboratory Press, Cold Spring Harbor, N.Y., 1989. Cells are genetically engineered by the introduction into the cells of heterologous DNA (RNA) encoding the sdp3.8 tumor associated polypeptide or fragment or variant thereof. The heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer,* 67:303–310, 1996). Also included are bacterial systems for delivery of antigens to eukaryotic cells, such as those which utilize *Yersinia* (e.g. Starnbach and Bevan, *J. Immunol.* 153:1603, 1994) and *Listeria* (Dietrich et al., *Nature Biotechnol.*16:181, 1998). Still other delivery and expression systems will be known to one of ordinary skill in the art.

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also permits the construction of tumor associate gene "knock-outs" in cells and in animals, providing materials for studying certain aspects of cancer and immune system responses to cancer.

The invention as described herein has a number of uses, some of which are described elsewhere herein. First, the invention permits isolation of the tumor associated protein molecules. A variety of methodologies well-known to the skilled practitioner can be utilized to obtain isolated tumor associated molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating tumor associated polypeptides. These include, but are not limited to, immunochromatography, HPLC, size-exclusion chromatography, ion-exchange chromatography and immune-affinity chromatography.

The isolation and identification of tumor associated nucleic acids also makes it possible for the artisan to diagnose a disorder characterized by expression of tumor associated nucleic acids or polypeptides. These methods involve determining expression of one or more tumor associated nucleic acids, and/or encoded tumor associated polypeptides and/or peptides derived therefrom. In the former situation, such determinations can be carried out via any standard nucleic acid determination assay, including the polymerase chain reaction, or assaying with labeled hybridization probes. In the latter situation, such determinations can be carried out by screening patient antisera for recognition of the polypeptide or by assaying biological samples with binding partners (e.g., antibodies) for tumor associated polypeptides or complexes of antigens derived therefrom and HLA molecules.

The invention also makes it possible isolate proteins which bind to tumor associated polypeptides as disclosed herein, including antibodies and cellular binding partners of the tumor associateds. Additional uses are described further herein.

The invention also provides, in certain embodiments, "dominant negative" polypeptides derived from tumor associated polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, one of ordinary skill in the art can modify the sequence of tumor associated polypeptides by site-specific mutagenesis, scanning mutagenesis, partial gene deletion or truncation, and the like. See, e.g., U.S. Pat. No. 5,580,723 and Sambrook et al., *Molecular Cloning: A Laboratory Manual,* Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art.

The invention also involves agents which bind to tumor associated polypeptides encoded by sdp3.8 nucleic acid molecules ("sdp3.8 polypeptides"), and in certain embodiments preferably to unique fragments of the sdp3.8 polypeptides. Such binding partners can be used in screening assays to detect the presence or absence of a sdp3.8 polypeptide and in purification protocols to isolate sdp3.8 polypeptides. Likewise, such binding partners can be used to selectively target drugs, toxins or other molecules to leukemia cells which present sdp3.8 tumor associated polypeptides. In this manner, cells present in solid or non-solid tumors which express sdp3.8 tumor associated polypeptides can be treated with cytotoxic compounds. Such agents also can be used to inhibit the native activity of the tumor associated polypeptides, for example, by binding to such polypeptides.

The invention, therefore, involves antibodies or fragments of antibodies having the ability to selectively bind to sdp3.8 tumor associated polypeptides, and preferably to unique fragments thereof. Antibodies include polyclonal and monoclonal antibodies, prepared according to conventional methodology.

The antibodies of the present invention thus are prepared by any of a variety of methods, including administering protein, fragments of protein, cells expressing the protein or fragments thereof and the like to an animal to induce polyclonal antibodies. The production of monoclonal antibodies is according to techniques well known in the art. As detailed herein, such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention also preferably are specific for the TRA/HLA complexes described herein.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies. Thus, the invention involves polypeptides of numerous size and type that bind specifically to tumor associated polypeptides including sdp3.8 polypeptides. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent a completely degenerate or biased array. One then can select phage-bearing inserts which bind to a sdp3.8 tumor associated polypeptide. This process can be repeated through several cycles of reselection of phage that bind to a sdp3.8 polypeptide. Repeated rounds lead to enrichment of phage bearing particular sequences. DNA sequence analysis can be conducted to identify the sequences of the expressed polypeptides. The minimal linear portion of the sequence that binds to the sdp3.8 polypeptide can be determined. One can repeat the procedure using a biased library containing inserts containing part or all of the minimal linear portion plus one or more additional degenerate residues upstream or downstream thereof. Thus, the tumor associated polypeptides of the invention can be used to screen peptide libraries, including phage display libraries, to identify and select peptide binding partners of the tumor associated polypeptides of the invention. Such molecules can be used, as described, for screening assays, for diagnostic assays, for purification protocols or for targeting drugs, toxins and/or labeling agents (e.g. radioisotopes, fluorescent molecules, etc.) to cells which express tumor associated genes such as those leukemia cells which present sdp3.8 polypeptides on the cell surface. Such binding agent molecules can also be prepared to bind complexes of an sdp3.8 polypeptide and an HLA molecule by selecting the binding agent using such complexes.

A tumor associated antigen polypeptide, or a fragment thereof, also can be used to isolate their native binding partners. Isolation of such binding partners may be performed according to well-known methods. For example, isolated tumor associated antigen polypeptides can be attached to a substrate (e.g., chromatographic media, such as polystyrene beads, or a filter), and then a solution suspected of containing the binding partner may be applied to the substrate. If a binding partner which can interact with tumor associated antigen polypeptides is present in the solution, then it will bind to the substrate-bound tumor associated antigen polypeptide. The binding partner then may be isolated.

As detailed herein, the foregoing antibodies and other binding molecules may be used for example to identify tissues expressing protein or to purify protein. Antibodies also may be coupled to specific diagnostic labeling agents for imaging of cells and tissues that express tumor associated polypeptides or to therapeutically useful agents according to standard coupling procedures. Diagnostic agents include, but are not limited to barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m. iodine-131 and indium-111, nuclides for nuclear magnetic resonance such as fluorine and gadolinium. Other diagnostic agents useful in the invention will be apparent to one of ordinary skill in the art. As used herein, "therapeutically useful agents" include any therapeutic molecule which desirably is targeted selectively to a cell expressing one of the cancer antigens disclosed herein, including antineoplastic agents, radioiodinated compounds, toxins, other cytostatic or cytolytic drugs, and so forth. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, pp.1202–1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or Pseudomonas exotoxin. Toxin moieties can also be high energy-emitting radionuclides such as cobalt-60.

The skilled artisan can determine which HLA molecule binds to tumor rejection antigens derived from sdp3.8 tumor rejection antigen precursors by, e.g., experiments utilizing antibodies to block specifically individual HLA class I molecules. For example, antibodies which bind selectively to HLA-A2 will prevent efficient presentation of TRAs specifically presented by HLA-A2. Thus, if TRAs derived from a tumor associated gene such as HAGE (sdp3.8) are presented by HLA-A2, then the inclusion of anti-HLA-A2 antibodies in an in vitro assay will block the presentation of these TRAs. An assay for determining the nature of the HLA molecule is found in International Application No. PCT/US96/04037. Briefly, in determining the HLA molecule type, inhibition experiments were carried out where the production of tumor necrosis factor (TNF) by cytotoxic T lymphocyte (CTL) clone 263/17 was tested in the presence of monoclonal antibodies directed against HLA molecules or against CD4/CD8 accessory molecules. Four monoclonal antibodies were found to inhibit the production of TNF by CTL 263/17: monoclonal antibody W6/32, which is directed against all HLA class I molecules (Parham et al.,*J. Immunol.* 123:342, 1979), antibody 31.23.2 which recognizes HLA-B and C molecules (Rebai et al., *Tissue Antigens* 22:107, 1983), antibody ME-1 which specifically recognizes HLA-B7 (Ellis et al., *Hum. Immunol.* 5:49, 1982) and antibody B9.4.1 against CD8. No inhibition was found with antibodies directed against HLA Class II DR molecules (L243: Lampson et al., *J. Immunol.* 125:293, 1980), against HLA-A3 (GAPA 3: Berger et al., *Hybridomna* 1:87, 1982) or against CD4 (13B.8.82). The conclusion was that CTL 263/17 was of the CDS type, and recognized an antigen presented by HLA-B7. Similar experiments using widely available anti-HLA antibodies can be performed to determine the nature of a HLA molecule which presents a HAGE antigen.

Thus isolated tumor associated polypeptide molecules when processed and presented as the TRA, or as complexes of TRA and HLA, such as HLA-A2, HLA-A26 or HLA-B7, etc. may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provoke a CTL response, or be cells which already express both molecules without the need for transfection. Vaccines also encompass naked DNA or RNA, encoding a tumor associated TRA or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745–1748, 1993).

When "disorder" is used herein, it refers to any pathological condition where the tumor rejection antigen precursor is expressed. An example of such a disorder is cancer, sarcomas and carcinomas in particular.

As used herein, a subject is a human, non-human primate, cow, horse, pig, sheep, goat, dog, cat or rodent. In all embodiments human tumor antigens and human subjects are preferred.

Samples of tissue and/or cells for use in the various methods described herein can be obtained through standard methods such as tissue biopsy, including punch biopsy and cell scraping, and collection of blood or other bodily fluids by aspiration or other methods.

In certain embodiments of the invention, an immunoreactive cell sample is removed from a subject. By "immunoreactive cell" is meant a cell which can mature into an immune cell (such as a B cell, a helper T cell, or a cytolytic T cell) upon appropriate stimulation. Thus immunoreactive cells include CD34+ hematopoietic stem cells, immature r cells and immature B cells. When it is desired to produce cytolytic T cells which recognize a tumor associated antigen, the immunoreactive cell is contacted with a cell which expresses a tumor no associated antigen under conditions favoring production, differentiation and/or selection of cytolytic T cells; the differentiation of the T cell precursor into a cytolytic T cell upon exposure to antigen is similar to clonal selection of the immune system.

Some therapeutic approaches based upon the disclosure are premised on a response by a subject's immune system, leading to lysis of antigen presenting cells, such as sarcoma or carcinoma cells which present one or more tumor associated antigens. One such approach is the administration of autologous CTLs specific to a tumor associated antigen/ MHC complex to a subject with abnormal cells of the phenotype at issue. It is within the skill of the artisan to develop such CTLs in vitro. An example of a method for T cell differentiation is presented in International Application number PCT/US96/05607. Generally, a sample of cells taken from a subject, such as blood cells, are contacted with a cell presenting the complex and capable of provoking CTLs to proliferate. The target cell can be a transfectant, such as a COS cell of the type described supra. These transfectants present the desired complex of their surface and, when combined with a CTL of interest, stimulate its proliferation. COS cells, such as those used herein are widely available, as are other suitable host cells. Specific production of a CTL is well known to one of ordinary skill in the art. The clonally expanded autologous CTLs then are administered to the subject.

Another method for selecting antigen-specific CTL clones has recently been described (Altman et al., *Science* 274:94–96, 1996; Dunbar et al., *Curr. Biol.* 8:413–416, 1998), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein.

To detail a therapeutic methodology, referred to as adoptive transfer (Greenberg, *J. Immunol.* 136(5): 1917, 1986; Riddel et al., *Science* 257: 238, 1992; Lynch et al, *Eur. J. Immunol.* 21: 1403–1410, 1991; Kast et al., *Cell* 59: 603–614, 1989), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a tumor associated gene sequence. Once cells presenting the relevant complex are identified via the foregoing screening methodology, they can be combined with a sample from a patient, where the sample contains CTLs. If the complex presenting cells are lysed by the mixed CTL, sample, then it can be assumed that a tumor associated gene derived TRA is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex. Chen et al., *Proc. Natl. Acad. Sci. USA* 88: 110–114 (1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. For example, nucleic acids which encode a sdp3.8 TRA may be operably linked to promoter and enhancer sequences which direct expression of the sdp3.8 TRA in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding sdp3.8 TRAs. Nucleic acids encoding a sdp3.8 TRA also may be inserted into a retroviral genome, thereby facilitating integration of the nucleic acid into the genome of the target tissue or cell type. In these systems, the gene of interest is carried by a microorganism, e.g., a Vaccinia virus retrovirus or the bacteria BCG, and the materials de facto "infect" host cells. The cells which result present the complex of interest, and are recognized by autologous CTLs, which then proliferate.

A similar effect can be achieved by combining a TRAP or a stimulatory fragment thereof with an adjuvant to facilitate incorporation into HLA presenting cells in vivo. The TRAP is processed to yield the peptide partner of the HLA molecule while the TRA is presented without the need for further processing. Generally, subjects can receive an intradermal injection of an effective amount of a sdp3.8 encoded TRAP, and/or TRAs derived therefrom. TRAs from sdp3.8 also can be combined with TRAs from other tumor associated polypeptides in a polytope arrangement as described above. Initial doses can be followed by booster doses, following immunization protocols standard in the art.

The invention involves the use of various materials disclosed herein to "immunize" subjects or as "vaccines". As used herein, "immunization" or "vaccination" means increasing or activating an immune response against an antigen. It does not require elimination or eradication of a condition but rather contemplates the clinically favorable enhancement of an immune response toward an antigen. Generally accepted animal models can be used for testing of immunization against cancer using a tumor associated antigen nucleic acid. For example, human cancer cells can be introduced into a mouse to create a tumor, and one or more tumor associated nucleic acids can be delivered by the methods described herein. The effect on the cancer cells (e.g., reduction of tumor size) can be assessed as a measure of the effectiveness of the tumor associated nucleic acid immunization. Of course, testing of the foregoing animal model using more conventional methods for immunization include the administration of one or more tumor associated polypeptides or peptides derived therefrom, optionally combined with one or more adjuvants and/or cytokines to boost the immune response. Methods for immunization, including formulation of a vaccine composition and selection of doses, route of administration and the schedule of administration (e.g. primary and one or more booster doses), are well known in the art. The tests also can be performed in humans, where the end point is to test for the presence of enhanced levels of circulating CTLs against cells bearing the antigen, to test for levels of circulating antibodies against the antigen, to test for the presence of cells expressing the antigen and so forth.

As part of the immunization compositions, one or more tumor associated polypeptides stimulatory fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., *Mol. Cells* 7:178–186, 1997); incomplete Freund's adjuvant; complete Freund's adjuvant; montanide; and various water-in-oil emulsions prepared from biodegradable oils such as squalene and/or tocopherol. Preferably, the peptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 $\mu$g to about 100 $\mu$g. Other adjuvants are known in the art and can be used in the invention (see, e.g. Goding, *Monoclonal Antibodies: Principles and Practice,* 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432–1434, 1995), GM-CSF and IL-18. Thus cytokines can be administered in conjunction with antigens and adjuvants to increase the immune response to the antigens.

There are a number of additional immune response potentiating compounds that can be used in vaccination protocols. These include costimulatory molecules provided in either protein or nucleic acid form. Such costimulatory molecules include the B7-1 and 137-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts width CTLA4 (CD 152) on T cells and studies involving CTLA4 and B7 ligands indicate that the B7-CTLA4 interaction can enhance antitumor immunity and CTL proliferation (Zheng et al., *Proc. Natl. Acad. Sci. USA* 95:6284–6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637–5648, 1995). Tumor cell transfection with B7 has been discussed in relation to in vitro CTL expansion for adoptive transfer immunotherapy by Wang et al. (*J. Immunother.* 19:1–8, 1996). Other delivery mechanisms for the B7 molecule would include nucleic acid (naked DNA) immunization (Kim et al., *Nature Biotechnol.* 15:7:641–646, 1997) and recombinant viruses such as adeno and pox (Wendtner et al., *Gene Ther.* 4:726–735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered.

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.,* 158:637–642, 1997; Fenton et al., *J. Immunother.,* 21:95–108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L, (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL,-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). In these situations Th help and B7 costimulation signals are not provided. This mechanism might be used in the context of antigen pulsed DC based therapies or in situations where Th epitopes have not been defined within known tumor associated antigen precursors.

The invention contemplates delivery of nucleic acids, polypeptides or peptides for vaccination. Delivery of polypeptides and peptides can be accomplished according to standard vaccination protocols which are well known in the art. In another embodiment, the delivery of nucleic acid is accomplished by ex vivo methods, i.e. by removing a cell from a subject, genetically engineering the cell to include a tumor associated nucleic acid, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo nucleic acid delivery using vectors such as viruses and targeted liposomes also is contemplated according to the invention.

In preferred embodiments, a virus vector for delivering a nucleic acid encoding a tumor associated polypeptide is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220–227, 1996; Eloit et al., *J. Virol.* 7:5375–5381, 1997; Chengalvala et al., *Vaccine* 15:335–339, 1997), a modified retrovirus (Townsend et al., *J. Virol.* 71:3365–3374, 1997), a nonreplicating retrovirus (Irwin et al., *J. Virol.* 68:5036–5044, 1994), a replication defective Semliki Forest virus (Zhao et al., *Proc. Natl. Acad. Sci. USA* 92:3009–3013, 1995), canarypox virus and highly attenuated vaccinia virus derivative (Paoletti, *Proc. Natl. Acad. Sci. USA* 93:11349–11353, 1996), non-replicative vaccinia virus (Moss, *Proc. Natl. Acad. Sci. USA* 93:11341–11348, 1996), replicative vaccinia virus (Moss, *Dev. Biol. Stand.* 82:55–63, 1994), Venzuelan equine encephalitis virus (Davis et al., *J. Virol.* 70:3781–3787, 1996), Sindbis virus (Pugachev et al., *Virology* 212:587–594, 1995), and Ty virus-like particle (Allsopp et al., *Eur. J. Immunol* 26:1951–1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Cliffton, N.J. (1991).

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection or infection with the foregoing viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Preferred antibodies include antibodies which selectively bind a tumor associated polypeptide, alone or as a complex with a MHC molecule. Especially preferred are monoclonal antibodies. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694–1712). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of stimulating an immune response, the desired response is an increase in antibodies or T lymphocytes which are specific for the immunogen(s) employed. These responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

According to another aspect of the invention, methods for diagnosing or determining the prognosis of a disorder that is characterized by expression of a HAGE (sdp3.8) tumor associated nucleic acid or polypeptide are provided. The methods involve contacting a biological sample isolated from a subject with an agent specific for the tumor associated nucleic acid or polypeptide to detect the presence of the tumor associated nucleic acid or polypeptide in the biological sample. Optionally, a series of tests is carried out over time to determine the subject's prognosis with respect to progression or regression of the disorder.

As used herein, "contacting" means placing the biological sample in sufficient proximity to the agent and under the appropriate conditions of, e.g., concentration, temperature, time, ionic strength, to allow the specific interaction between the agent and tumor associated nucleic acid or polypeptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The biological sample can be located in vivo or in vitro. For example, the biological sample can be a tissue in vivo and the agent specific for the tumor associated nucleic acid or polypeptide can be used to detect the presence of such molecules in the hematopoietic tissue (e.g., for imaging portions of the tissue that express the tumor associated gene products). Alternatively, the biological sample can be located in vitro (e.g., a blood sample, tumor biopsy, tissue extract). In a particularly preferred embodiment, the biological sample can be a cell-containing sample, more preferably a sample containing tumor cells.

EXAMPLES

Example 1

Isolation of a Nucleic Acid Specifically Expressed by Sarcoma Cell Line LB-23

Specific cDNA fragments of sarcoma cell line LB-23 were enriched by subtraction of cDNA fragments found in normal uterus, breast, colon and heart, according to the representational difference analysis method (RDA) described for cDNA by Hubank & Schatz (*Nucl. Acids Res.* 22:5640, 1994).

Briefly, cellular cDNAs obtained by reverse transcription with an oligo-dT primer on poly-A RNA of the normal and sarcoma cell samples were digested by restriction enzyme DpnII. The DpnII fragments of each origin were ligated with the same set of adapters, divided in several groups and separately amplified by PCR. The PCR products originating from the same sample were pooled and digested again by DpnII. The DpnII fragments from the sarcoma cell line (the tester) were ligated with a new adapter set and hybridized with an excess of DpnII fragments derived from the normal tissues (the driver). The hybridization mixture was then submitted to PCR amplification using the new adapter set. Only those DpnII fragments derived from the tester and absent in the driver were expected to be amplified exponentially because they carry primer-complementary sequences at both ends. Three cycles of subtractive hybridization and amplification were performed. The final PCR mixture products were then cloned and sequenced.

The sequencing of 106 cDNA clones yielded 42 different sequences. Twenty-seven sequences corresponded to genes recorded in databases: most of these genes are involved in cell proliferation, whereas the remaining genes are ectopically expressed differentiation genes, mitochondrial genes, oncogenes, or genes with unknown function. Fifteen cDNA clones showed no homology to any recorded gene. Among the 15 unknown sequences, one, named sdp3.8, appeared to have tumor associated expression as seen by RT-PCR. The sequence of the sdp3.8 clone was 323 bp long (SEQ ID NO:1). The sdp3.8 cDNA nucleotide sequence has four open reading frames (ORFs) beginning at nucleotides 27 (12 amino acids), 103 (35 amino acids), 170 (50 amino acids) and 210 (36 amino acids). The amino acid sequences of the ORFs are set forth in SEQ ID NOs:38–41, respectively.

Example 2

Expression of Gene sdp3.8 in Normal Tissues and Tumor Samples

The expression pattern of the sdp3.8 messenger was determined by RT-PCR analysis of normal tissues and tumor samples. Two primers were selected for PCR analysis: a sense primer, sdp3.8S (5'-TAGAGAGGAAGGTTTGAAAT-3'; SEQ ID NO:2), located at nucleotides 9–28 of SEQ ID NO:1, and an antisense primer, sdp3.8A (5'-ATGTGCAGGTAGATTGGGAT-3'; SEQ ID NO:3), located at nucleotides 187–206 of SEQ ID NO: 1. Total RNA of normal or tumor samples of the indicated origins were converted to cDNA. The cDNA corresponding to 50 ng of total RNA was then amplified by PCR with primers sdp3.8S and sdp3.8A with 0.625U of TaKaRa Taq polymerase for 30 cycles (94° C. 1 min; 57° C., 2 min; 72° C., 2 min) with 15' at 72° C. for the final extension. The PCR using the same primers also was performed using genomic DNA as a substrate. The primers are located in different exons, as determined by the different sizes of PCR products obtained on cDNA (196 bp) or genomic DNA (approximately 3 kb).

Sdp3.8 is not expressed in a panel of normal tissues tested (Table II), with the exception of testis. Thus sdp3.8 shares an expression pattern with other tumor associated genes in that it is expressed only in immune privileged normal tissues such as testis. Among tumoral samples (Table III), sdp3.8 is frequently expressed in sarcomas (32%). Sdp 3.8 is expressed with lesser frequency in epidermoid carcinoma (10%). non-small cell lung carcinoma (7%), head & neck carcinoma (5%), brain tumors, neuroblastoma and uveal melanoma tumor samples.

TABLE II

Expression of gene sdp3.8 in normal tissues (RT-PCR)

| Tissue Sample | code | detection of sdp3.8 |
|---|---|---|
| ovary | CLO7 | — |
| kidney | BA21 | — |
| kidney | BA4 | — |
| adrenal glands | LB539 | — |
| adrenal glands | LB538 | — |
| uterus | LB1022 | — |
| breast | LB673 | ± |
| breast | LB520 | — |
| sperm | LB568 | — |
| skin | LB243 | — |
| skin | LB148 | — |
| brain | JNO9 | — |
| testis | LB882 | +++ |
| testis | LB881 | +++ |
| heart | CLO3 | — |
| prostate | CLO9 | — |
| stomach | LB189 | — |
| lung | LB264 | — |
| lung | LB176 | — |
| colon | LB298 | — |
| bladder | HM83 | — |
| liver | LB898 | — |
| liver | CLO10 | — |
| bone marrow | LB1039 | — |
| PBL | LB490 | — |
| retina | SH8 | — |

TABLE III

Expression of gene sdp3.8 in tumors (RT-PCR)

| Sample | number | sdp3.8 positive | (%) |
|---|---|---|---|
| Cutaneous melanoma | 47 | 0 | |
| Primary | 25 | 0 | |
| Metastatic | 22 | 0 | |
| Uveal melanoma | 5 | 1 | |
| Neuroblastoma | 2 | 1 | |
| Bladder carcinoma | 30 | 0 | |
| Breast carcinoma | 14 | 0 | |
| Lung carcinoma NSCLC | 27 | 2 | 7% |
| Epidermoid carcinoma | 20 | 2 | 10% |
| Bronchiolo-alveolar carcinoma | 2 | 0 | |
| Adenocarcinoma | 13 | 0 | |
| Sarcoma | 19 | 6 | 32% |
| Brain tumors | 6 | 1 | |
| Prostate adenocarcinoma | 2 | 0 | |
| Head & neck carcinoma | 20 | 1 | 5% |
| Colorectal carcinoma | 19 | 0 | |
| Leukemia | 25 | 0 | |
| Renal tumors | 16 | 0 | |
| Uterine tumors | 5 | 0 | |
| Esophageal carcinoma | 14 | 0 | |
| Myeloma | 5 | 0 | |
| Mesothelioma | 4 | 0 | |
| Thyroid | 5 | 0 | |

Example 3

Isolation of a Full Length sdp3.8 cDNA Clone

To obtain the complete sdp3.8 cDNA, a classical cDNA library was screened with a sdp3.8 probe. The cDNA library was constructed with LB451 testis RNA in pcDNA1/Amp as described for SK29-MEL.1 RNA in U.S. Pat. No. 5,519,117. Approximately 250,000 bacteria were plated on nylon membranes. Duplicates were made and treated to denature and fix the bacterial DNA. A sdp3.8 specific probe was generated by performing RT-PCR (reverse transcription-PCR) using LB23-SARC RNA as template and sdp3.8 specific primers as described above. The 196 bp sdp3.8 PCR product was purified on a sepharose CL-6B column, then labeled using random primers, Klenow DNA polymerase and α-$^{32}$-P-dCTP according to standard procedures. Treated duplicate nylon membranes were hybridized with the sdp3.8 specific probe (overnight incubation at 65° C.), then washed in stringent conditions, and autoradiographed overnight. Positive spots were obtained. A secondary screening was performed according to standard procedures, and a bacterial clone was obtained which contained the complete sdp3.8 cDNA. The complete sdp3.8 cDNA clone was sequenced and found to be 2365 nucleotides long (SEQ ID NO:42) inclusive of the poly A tail, or about 2340 nucleotides long without the poly A tail. An open reading frame runs through the cDNA, with the first ATG at nucleotide 208 and a stop codon at nucleotide 2152. It encodes a putative protein of 648 amino-acids (SEQ ID NO:43). The gene was found to have homology to p68 RNA helicase, and so was called HAGE, for Helicase-related AntiGEn.

Example 4

Identification of the Portion of Tumor Associated Genes Encoding Tumor Rejection Antigens In a first method, available CTL clones directed against antigens presented by autologous tumor cells shown to express one or more of the tumor associated genes are screened for specificity against COS cells transfected with sdp3.8 genes and autologous HLA alleles as described by Brichard et al. (*Eur. J. Immunol.* 26:224–230, 1996). CTL recognition of sdp3.8 is determined by measuring release of TNF from the cytolytic T lymphocyte or by $^{51}$Cr release assay (Herin et al., *Int. J. Cancer* 39:390–396, 1987). If a CTL clone specifically recognizes a transfected COS cell, shorter fragments of the coding sequences are prepared and tested by transfecting COS cells to identify the region of the gene that encodes the peptide recognized by the CTL. Fragments of sdp3.8 are prepared by exonuclease III digestion or other standard molecular biology methods such as PCR. Synthetic peptides are prepared and tested to confirm the exact sequence of the antigen.

Alternatively, CTL clones are generated by stimulating the peripheral blood lymphocytes (PBLs) of a patient with autologous normal cells transfected with DNA clones encoding sdp3.8 polypeptides (e.g. SEQ ID NO:1) or with irradiated PBLs loaded with synthetic peptides corresponding to the putative proteins and matching the consensus for the appropriate HLA class I molecule to localize the antigenic peptide within the sdp3.8 clones (see, e.g., van der Bruggen et al., *Eur. J. Immunol.*24:3038–3043, 1994; Herman et al., Immunogenetics 43:377–383, 1996). Localization of one or more antigenic peptides in a protein sequence can be aided by HLA peptide binding predictions made according to established rules for binding potential (e.g., Parker et al, *J. Immunol.* 152:163 , 1994; Rammensee et al., *Immunogenetics* 41:178–228, 1995). HLA binding predictions can conveniently be made using an algorithm available via the Internet on the National Institutes of Health World Wide Web site at URL http://bimas.dcrt.nih.gov. For example, several predicted HLA binding motifs for the four potential sdp3.8 ORFs based on SEQ ID NO:1 (SEQ ID Nos:38–41) or the long open reading frame (SEQ ID NO:43) of the HAGE cDNA (SEQ ID NO:42) are listed in the table below:

TABLE IV

Predicted HLA binding motifs in HAGE (sdp3.8) polypeptides

| SEQ ID NO/amino acids | HLA molecule | Binding score (t½ disassociation) |
| --- | --- | --- |
| SEQ43/AA297–305 | A_0201 | 746 |
| SEQ43/AA380–388 | A3 | 180 |
| SEQ40/AA19–27 | A24 | 126 |
| SEQ43/AA44–52 | A68.1 | 400 |
| SEQ43/AA489–497 | A68.1 | 240 |
| SEQ40/AA2–10 | B7 | 200 |
| SEQ41/AA2–10 | B7 | 80 |
| SEQ43/AA29–37 | B_2705 | 3000 |
| SEQ43/AA435–443 | B_2705 | 2000 |
| SEQ41/AA27–35 | B_2705 | 2000 |
| SEQ43/AA17–25 | B_2705 | 1000 |
| SEQ41/AA8–16 | B_2705 | 1000 |
| SEQ41/AA16–24 | B_2705 | 600 |
| SEQ41/AA15–23 | B_2705 | 600 |
| SEQ39/AA24–32 | B44 | 420 |
| SEQ40/AA24–32 | B44 | 90 |
| SEQ39/AA27–35 | Cw_0301 | 125 |

Alternatively, CTL clones obtained by stimulation of lymphocytes with autologous tumor cells which express sdp3.8 are screened for specificity against COS cells transfected with sdp3.8 cDNA and autologous HLA alleles as described by Brichard et al. (*Eur. J. Immunol.* 26:224–230, 1996).

Optionally, shorter fragments of HAGE/sdp3.8 cDNAs are generated by PCR. Shorter fragments are used to provoke TNF release or $^{51}$Cr release as above.

Example 5

Identification of Tumor Associated Gene Encoded Tumor Rejection Antigen Peptides Synthetic peptides corresponding to portions of the shortest fragment of sdp3.8 which provokes TNF release are prepared. Progressively shorter peptides are synthesized to determine the optimal sdp3.8 tumor rejection antigen peptides for a given HLA molecule.

Synthetic peptides are tested for lysis of HLA expressing cells according to known procedures. For example, if the HLA which presents a peptide of interest is determined to be HLA-A2, then T2 cells can be used. T2 cells are HLA-A2$^+$ cells which have an antigen-processing defect resulting in an increased capacity to present exogenous peptides. T2 cells are mixed with a synthetic peptide corresponding to the CTL-reactive portion of sdp3.8. CTL cells are added and lysis is measured after 4 hours to determine which peptides efficiently stimulate the lysis of T2 cells bearing HLA-A2. Other HLA expressing cells are known in the art or can be prepared by transfection with specific HLA clones.

To determine the optimal size of the synthetic peptide, peptides of decreasing size are synthesized based on the sequence of the peptide determined above, by successively removing one amino acid from the amino terminal end or the carboxy terminal end of the peptide. These peptides are tested for the ability to induce cell lysis of appropriate HLA expressing cells by CTL cells in a dose response assay. Lyophilized peptides are dissolved at 20 mg/ml in DMSO, then diluted to 2 mg/mil in 10 mM acetic acid and stored at −80° C. Target cells, e.g. HLA-A2+ T2 cells, are labeled with $^{51}$Cr, as described above, for 1 hour at 37° C. followed extensive washing to remove unincorporated label. To confirm the necessity of the interaction of the peptide with the HLA, T2 cells optionally can be pretreated with an anti-HLA-A2 antibody, such as MA2.1 (Wolfel et al., *Eur. J. Immunol.* 24: 759–764, 1994), and then are incubated in 96-well microplates in the presence of various concentrations of peptides for 30 minutes at 37° C. CTLs which recognize the peptide presented by the HLA are then added in an equal volume of medium at an effector:target ratio of 30:1. Chromium-51release is measured after 4 hours.

Example 6

Normal Cells are not Lysed by CTLs Which Lyse Cells Expressing Tumor Associated Genes This example describes CTL lysis experiments with various cell lines with or without incubation with the tumor associated gene derived peptides determined above. Tumor cells which express sdp3.8, normal B cells transformed with EBV (B-EBV) from the patient who is the source of the tumor cells, and normal peripheral blood lymphocytes from the same patient (PBL) are tested for lysis by CTL cells in a dose response assay. These cells are incubated with CTLs at the effector/target ratios determined to be optimal in the dose response assays detailed above, and assayed for lysis as described above. Lysis of only the sdp3.8-expressing tumor cells by the CTLs, demonstrates that B-EBV and PBL cells of the patient are not recognized by the CTLs because such cells do not normally express the tumor rejection antigen derived from sdp3.8 proteins.

It is next determined whether these cells would be lysed by CTL if pulsed with a peptide derived from sdp3.8. The peptides selected on the basis of the experiments above are tested for the ability to induce cell lysis of sdp3.8-expressing tumor cells, B-EBV cells, and non-autologous cells which express the appropriate HLA by CTL cells in a dose response assay as in previous examples. B-EBV and PBL pulsed with preferred peptides are now lysed by CTLs, as are sdp3.8-expressing tumor cells and the non-autologous cells pulsed with preferred peptides.

TABLE V

HAGE (sdp3.8) Sequence Homologies (GenBank accession numbers)

AF018044, U60880, L22944, U85943, U89924, AF073995, AF019886, X90639, U52949, AF033115, U93301, AF018052, AF018056, U93295, L39119, U60876, Y10545, U65226, D44443, AJ000542, AF018066, X74324, AJ005168, AF018036, U60877, AF018053, D88984, U93302, U89672, AJ001134, U14118, AF018054, U93294, AC005501, AF046856, Y17556, AJ010397, AF018071, AF033196, AF045229, AF013625, AF015523, U93712, AF073473, AJ001044, AF019671, AF019720, AF041461, U15425, AJ006789, D16247, D49729, L33810, U31958, AC005372, U92795, AF011925, AF056022, AF054142, AF019721, U36623, AF028729, U67221, U13667, AB010259, U25746, U46006, U89673, U83666, Z46845, AF030780, U13563, AF034540, AF048848, AF054140, U90261, AF034793, AF030777, AF075440, J04847, AF034805, AF034539, AF030779, AF021811, AF054065, AF019734, U89574, AF054135, Z12125, U58669, U82970, U37222, AF053372, AF030774, Y16911, L38622, AF056702, X65627, AF030773, U00031, X57328, AB008265, AF000984, M83211, L25126, AF045381, Z38117, AB003909, AF000985, L08427, AC004120, Z54202, U93298, U49757, Y16912, X85122, AF018055, Z77249, AF000982, AF000983, U50553, AF061337, U32699, AC002483, Z83822, AE001174, AA883800, AA948168, R82515, F20206, F20451, F20430, F20197, F20205, AA514191, F20377, F20455, F20201, F20494, F20380, F20443, AA514190, F20198, F20182, F20192, F20472, F20456, F20460, F20484, F20187, F20189, F20495, F20208, F20446, F20373, F20471, F20468, F20457, F20404, F20490, F20412, F20212, F20449, F20461, F20499, F20450, F20376, F20464, F20487, F20188, F20459, F20193, F20486, F20448, F20407, F20194, F20497, F20502, F20181, F20508, F20453, F20374, F20209, F20509, F20389, AA933999, F20485, F20214, F20410, F20388, F20500, F20470, F20406, F20386, F20213, F20488, F20190, F20203, F20199, F20431, F20180, F20191, F20408, F20489, F20196, F20387, F21475, F21480, F20379, F20507, F20503, F20465, F20382, F20204, F20381, F20411, F20416, F20215, F20458, F20419, F20447, F20378, F20462, F20216, F20429, F20210, F20418, F20385, F20384, F20383, F20505, F20202, F20498, F20207, F20218, F20445, F20454, F20463, F20390, F20501, F22435, F20195, F20220, AA996393, F20375, H43402, H30783, AA356553, R82572, R13011, AA643791, F20405, T85890, T82153, AA316798, AA248948, H65151, AA883852, A1018020, R18664, R46313, A1050031, T89754, AA070542, H04357, AA148692, AF037645, AA453316, AA573298, W52969, AA591070, U24210, W91597, W91767, W91680, AA681183, AA166485, AA920867, AA120483, AA574856, AA895748, AA144517, AA983064, AA124406, AA116852, AA199025, AA791735, W29675, AA105648, AA645800, AA020429, AA541947, AA709485, AA174503, AA172504, AA086670, AF027363, AF064731, AF062411, AF064739, U83604, U19683, AA514079, A1137622, F20150, A1099575, A1043754, A1028830, Z30733, A1010783, N82908, C91736, AA440301, T41860, AA395139, AA849867, A1008158, AA851373, A1007729, AA042545.

The terms and expressions which have been employed are used as terms of description and not of limitation, and there is no intention in the use of such terms and expressions of excluding any equivalents of the features shown and described or portions thereof, it being, recognized that various modifications are possible within the scope of the invention.

All of the references described herein are incorporated by reference.

We claim:

1. An isolated antibody or binding fragment thereof which selectively binds a protein encoded by an isolated nucleic acid molecule selected from the group consisting of (a) nucleic acid molecules which hybridize under stringent conditions to a complement of a nucleic acid molecule having a nucleotide sequence set forth as SEQ ID NO:42, and which code for a sarcoma associated gene product, wherein the stringent conditions are hybridization at 65° C. in hybridization buffer (3.5×SSC, 0.02% Ficoll, 0.02% polyvinyl pyrrolidone, 0.02% Bovine Serum Albumin, 25 mM $NaH_2PO_4$ (pH 7), 0.5% SDS, 2 mM EDTA) and wherein SSC is 0.15M sodium chloride/0.015M sodium citrate, pH 7; SDS is sodium dodecyl sulphate; and EDTA is ethylenediaminetetracetic acid, and (b) nucleic acid molecules that differ from the nucleic acid molecules of (a) in codon sequence due to the degeneracy of the genetic code.

2. The isolated antibody or binding fragment thereof of claim 1, wherein the isolated antibody or binding fragment thereof is a fragment of an antibody selected from the group consisting of Fab fragments, $F(ab)_2$ fragments, Fv fragments and fragments including a CDR3 region selective for the protein.

3. The isolated antibody or binding fragment thereof of claim 1, wherein the isolated antibody or binding fragment thereof is an antibody selected from the group consisting of monoclonal antibodies, humanized antibodies, single chain antibodies and chimeric antibodies.

4. The isolated antibody or binding fragment thereof of claim 1, wherein the protein is encoded by an isolated nucleic acid molecule comprising a nucleotide sequence set forth as SEQ ID NO:1.

5. The isolated antibody or binding fragment thereof of claim 4, wherein the isolated antibody or binding fragment thereof is a fragment of an antibody selected from the group consisting of Fab fragments, $F(ab)_2$ fragments, Fv fragments and fragments including a CDR3 region selective for the protein.

6. The isolated antibody or binding fragment thereof of claim 4, wherein the isolated antibody or binding fragment thereof is an antibody selected from the group consisting of monoclonal antibodies, humanized antibodies, single chain antibodies and chimeric antibodies.

7. The isolated antibody or binding fragment thereof of claim 1, wherein the protein is encoded by an isolated nucleic acid molecule comprising the nucleic acid sequence set forth as nucleotides 208–2151 of SEQ ID NO:42.

8. The isolated antibody or binding fragment thereof of claim 7, wherein the isolated antibody or binding fragment thereof is a fragment of an antibody selected from the group consisting of Fab fragments, $F(ab)_2$ fragments, Fv fragments and fragments including a CDR3 region selective for the protein.

9. The isolated antibody or binding fragment thereof of claim 7, wherein the isolated antibody or binding fragment thereof is an antibody selected from the group consisting of monoclonal antibodies, humanized antibodies, single chain antibodies and chimeric antibodies.

10. The isolated antibody or binding fragment thereof of claim 1, wherein the protein is encoded by an isolated nucleic acid molecule comprising the nucleic acid sequence set forth as SEQ ID NO:42.

11. The isolated antibody or binding fragment thereof of claim 10, wherein the isolated antibody or binding fragment thereof is a fragment of an antibody selected from the group consisting of Fab fragments, $F(ab)_2$ fragments, Fv fragments and fragments including a CDR3 region selective for the protein.

12. The isolated antibody or binding fragment thereof of claim 10, wherein the isolated antibody or binding fragment thereof is an antibody selected from the group consisting of monoclonal antibodies, humanized antibodies, single chain antibodies and chimeric antibodies.

13. The isolated antibody or binding fragment thereof of claim 1, wherein the antibody or binding fragment thereof selectively binds an unique fragment of the protein, wherein the unique fragment is at least 9 amino acids in length.

14. The isolated antibody or binding fragment thereof of claim 13, wherein the isolated antibody or binding fragment thereof is a fragment of an antibody selected from the group consisting of Fab fragments, $F(ab)_2$ fragments, Fv fragments and fragments including a CDR3 region selective for the protein.

15. The isolated antibody or binding fragment thereof of claim 13, wherein the isolated antibody or binding fragment thereof is an antibody selected from the group consisting of monoclonal antibodies, humanized antibodies, single chain antibodies and chimeric antibodies.

16. An isolated antibody or binding fragment thereof which selectively binds a protein encoded by an isolated nucleic acid molecule selected from the group consisting of (a) an unique fragment of the nucleotide sequence set forth as nucleotides 1–2340 of SEQ ID NO:42, wherein the unique fragment is between 28 and 2339 nucleotides in length, and (b) complements of (a), provided that the nucleic acid molecules exclude sequences consisting only of those sequence provided in GenBank accession numbers AA883800 or AA948168.

17. The isolated antibody or binding fragment thereof of claim 16, wherein the isolated antibody or binding fragment thereof is a fragment of an antibody selected from the group consisting of Fab fragments, $F(ab)_2$ fragments, Fv fragments and fragments including a CDR3 region selective for the protein.

18. The isolated antibody or binding fragment thereof of claim 16, wherein the isolated polypeptide is an antibody selected from the group consisting of monoclonal antibodies, humanized antibodies, single chain antibodies and chimeric antibodies.

* * * * *